US012590095B2

(12) United States Patent
Adamer et al.

(10) Patent No.: US 12,590,095 B2
(45) Date of Patent: Mar. 31, 2026

(54) CRYSTALLINE FORMS OF AN ORALLY AVAILABLE, SELECTIVE KIT AND PDGFR KINASE INHIBITOR

(71) Applicant: Sandoz AG, Basel (CH)

(72) Inventors: Verena Adamer, Kundl (AT); Andrea Thaler, Kundl (AT); Erwin Schreiner, Kundl (AT)

(73) Assignee: SANDOZ AG, Basel (CH)

( * ) Notice: Subject to any disclaimer, the term of this patent is extended or adjusted under 35 U.S.C. 154(b) by 993 days.

(21) Appl. No.: 17/625,138

(22) PCT Filed: Jul. 2, 2020

(86) PCT No.: PCT/EP2020/068704
§ 371 (c)(1),
(2) Date: Jan. 6, 2022

(87) PCT Pub. No.: WO2021/004895
PCT Pub. Date: Jan. 14, 2021

(65) Prior Publication Data

US 2022/0267334 A1 Aug. 25, 2022

(30) Foreign Application Priority Data

Jul. 9, 2019 (EP) .................................... 19185144
Sep. 27, 2019 (EP) .................................... 19200036
Feb. 5, 2020 (EP) .................................... 20155582

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
CPC .................................................... C07D 487/04
USPC .......................................................... 514/243
See application file for complete search history.

(56) References Cited

U.S. PATENT DOCUMENTS

2021/0147433 A1 5/2021 Waetzig et al.

FOREIGN PATENT DOCUMENTS

CN 109970745 A * 7/2019 ............. A61K 45/06
WO WO-2015057873 A1 * 4/2015 .............. A61P 35/00
WO WO-2020210669 A1 * 10/2020 ........... C07D 487/04

OTHER PUBLICATIONS

Wang et al., Espacenet English translation of CN 109970745 A claims, 2019 (Year: 2019).*
Byrn, Stephen, et al., Pharmaceutical Solids: A Strategic Approach to Regulatory Considerations. Pharm Res 12 (7), 1995, pp. 945-954.
Caira, Mino R., Topics in Current Chemistry, vol. 198, 1998, pp. 163-208.
International Search Report and Written Opinion for PCT/EP2020/068704, date of mailing Oct. 14, 2021, 10 pages.
Pecharsky, et al., Fundamentals of powder diffraction and structural characterization of materials, 2005, Springer, p. 3.
Sheldrick, George M., Acta Cryst. A71, 2015, pp. 3-8.
Sheldrick, George M., Acta Cryst. C71, 2015, pp. 3-8.
English translation of text of first Office Action, Chinese patent application 202080062947.9.

* cited by examiner

*Primary Examiner* — Jeffrey H Murray
*Assistant Examiner* — Rilla Marie Samsell
(74) *Attorney, Agent, or Firm* — Myers Bigel, P.A.

(57) ABSTRACT

The present invention relates to crystalline avapritinib, polymorphs and hydrates thereof as well as to processes for their preparation. Furthermore, the invention relates to a pharmaceutical composition comprising crystalline avapritinib and at least one pharmaceutically acceptable excipient. The pharmaceutical composition of the present invention can be used as a medicament, in particular for the treatment of patients with gastrointestinal stromal tumors (GIST) and advanced systemic mastocytosis (AdvSM), including aggressive systemic mastocytosis (ASM), systemic mastocytosis with an associated hematologic neoplasm (SM-AHN) and mast cell leukemia (MCL).

15 Claims, 17 Drawing Sheets

CRYSTALLINE FORMS OF AN ORALLY AVAILABLE, SELECTIVE KIT AND PDGFR KINASE INHIBITOR

This application is a Section 371 national phase entry of PCT application PCT/EP2020/068704, filed Jul. 2, 2020. This application also claims the benefit of the earlier filing dates of European patent application 19185144.3, filed Jul. 9, 2019, European patent application 19200036.2, filed Sep. 27, 2019, and European patent application 20155582.8, filed Feb. 5, 2020.

FIELD OF THE INVENTION

The present invention relates to crystalline avapritinib, polymorphs and hydrates thereof as well as to processes for their preparation. Furthermore, the invention relates to a pharmaceutical composition comprising crystalline avapritinib and at least one pharmaceutically acceptable excipient. The pharmaceutical composition of the present invention can be used as a medicament, in particular for the treatment of patients with gastrointestinal stromal tumors (GIST) and advanced systemic mastocytosis (AdvSM), including aggressive systemic mastocytosis (ASM), systemic mastocytosis with an associated hematologic neoplasm (SM-AHN) and mast cell leukemia (MCL).

BACKGROUND OF THE INVENTION

Avapritinib is an orally available selective inhibitor of KIT and PDGFR kinase optionally featuring mutations in the activation loop and is currently being investigated for use in the treatment of patients with gastrointestinal stromal tumors (GIST) and advanced systemic mastocytosis (AdvSM), including aggessive systemic mastocytosis (ASM), systemic mastocytosis with and associated hematologic neoplasm (SM-AHN) and mast cell leukemia (MCL).

Avapritinib is chemically designated as (1S)-1-(4-fluorophenyl)-1-(2-[4-[6-(1-methyl-1H-pyrazol-4-yl)pyrrolo[2,1-f][1,2,4]triazin-4-yl]piperazin-1-yl]pyrimidin-5-yl)ethan-1-amine and can be represented by the chemical structure as depicted in Formula (I)

Formula (I)

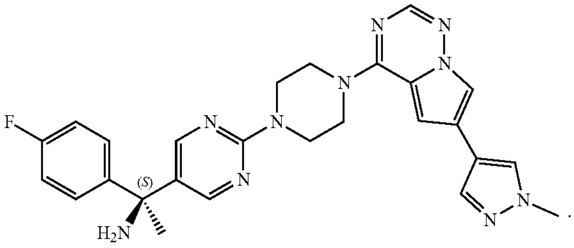

The compound avapritinib is disclosed in WO 2015/057873 A1, as compound 44, and is characterized by its $^{1}$H-NMR spectrum measured in DMSO-d6 and molecule mass determined by mass spectroscopy.

Different solid state forms of an active pharmaceutical ingredient often possess different properties. Differences in physicochemical properties of solid forms can play a crucial role for the improvement of pharmaceutical compositions, for example, pharmaceutical formulations with improved dissolution profile or with improved stability or shelf-life can become accessible due to an improved solid state form of an active pharmaceutical ingredient. Also processing or handling of the active pharmaceutical ingredient during the formulation process may be improved. New solid state forms of an active pharmaceutical ingredient can thus have desirable processing properties. They can be easier to handle, better suited for storage, and/or allow for better purification.

The tendency of a drug substance to absorb water from the environment can negatively affect the pharmaceutical behavior and quality of a drug product. Water absorption for example can lead to chemical degradation trigger changes of the physical form (e.g. via hydrate formation), lead to changes in dissolution behavior and influence powder properties such as flowability, compactability, tableting and compression behavior etc.

Furthermore, the sudden appearance or disappearance of a metastable polymorph can present a problem in process development. Similarly, serious pharmaceutical consequences arise if solid state transformations occur in a dosage form.

There is thus a need to provide a solid state form of avapritinib which possesses physicochemical properties allowing for the reliable production of a safe and efficacious drug product comprising avapritinib. In particular, there is a need for a solid state form of avapritinib which is stable upon storage of the active pharmaceutical ingredient, during formulation of a pharmaceutical drug product containing avapritinib and throughout the whole shelf-life of the drug product comprising avapritinib. Moreover, the provision of a non-hygroscopic or slightly hygroscopic solid state form of avapritinib would facilitate formulation and storage of avapritinib and drug products comprising avapritinib.

SUMMARY OF THE INVENTION

The present invention solves one or more of the above mentioned problems by providing avapritinib in crystalline form, in particular by providing polymorphs of avapritinib which are hereinafter also referred to as "Form A" and "Form B". Form A and Form B of avapritinib of the present invention both possess favorable physicochemical properties for a drug substance intended for use in an oral solid dosage form. Said properties concern chemical stability, physical stability, hygroscopicity, solubility, dissolution, morphology, crystallinity, flowability, compactibility and wettability.

In particular, crystalline avapritinib according to the present invention, in particular crystalline Form A and Form B of avapritinib of the present invention, possess physical properties allowing for the reliable production of a safe and efficacious pharmaceutical drug product, e.g. a solid dosage form such as a capsule or a tablet comprising avapritinib. In particular, the avapritinib crystals of the present invention are stable and preserve their crystal structures during manufacture and storage of a solid dosage form comprising avapritinib. For example, crystalline Form A and Form B of the present invention, are thermally stable against temperature stress e.g. they do not show any thermal events in the DSC curve up to a temperature of about about 180° C. and 190° C. when measured at a heating rate of 10 K/min, respectively. Moreover, both anhydrous forms are stable against temperature and moisture stress. In addition, they are non-hygroscopic or only slightly hygroscopic and preserve their crystal structures regardless relative humidity of the environment. For example, both forms are stable at a relative humidity range of about 0 to 90%, when measured with GMS at (25.0±1.0)° C. While both forms are kinetically stable, Form A is thermodynamically more stable compared to Form B.

One or more of the above mentioned problems may also be solved by providing hydrates of avapritinib, in particular by providing the hydrate of avapritinib hereinafter also referred to as "Form Hy1". For example, Form Hy1 of the present invention was found to be only slightly hygroscopic and to preserve its crystal structure when subjected to atmospheres having a relative humidity in the range of about 10 to 90%, when measured with GMS at (25.0±1.0)° C. Furthermore, Form Hy1 is physically and chemically stable when suspended in aqueous media and possesses an advantageous solubility and dissolution profile. Last but not least Form Hy1 is stable against temperature and moisture stress.

Abbreviations

PXRD powder X-ray diffractogram
SXRD single X-ray diffraction
DSC differential scanning calorimetry
TGA thermogravimetric analysis
GMS gravimetric moisture sorption
FTIR Fourier transform infrared
RT room temperature
RH relative humidity
API active pharmaceutical ingredient
KIT V-Kit Hardy Zuckermann 4 Feline Sarcoma Viral Oncogene Homolog
PDFGR platelet-derived growth factor receptor
w-% weight percent
THF tetrahydrofuran

Definitions

As used herein the term "room temperature" refers to a temperature in the range of from 20 to 30° C.

The term "avapritinib" as used herein refers to (1S)-1-(4-fluorophenyl)-1-(2-[4-[6-(1-methyl-1H-pyrazol-4-yl)pyrrolo[2,1-f][1,2,4]triazin-4-yl]piperazin-1-yl]pyrimidin-5-yl) ethan-1-amine according to the chemical structure depicted in Formula (I) disclosed herein above.

As used herein, the term "measured at a temperature in the range of from 20 to 30° C." refers to a measurement under standard conditions. Typically, standard conditions mean a temperature in the range of from 20 to 30° C., i.e. at room temperature. Standard conditions can mean a temperature of about 22° C. Typically, standard conditions can additionally mean a measurement at 20-70% relative humidity, preferably at 30-60% relative humidity.

The term "reflection" with regard to powder X-ray diffraction as used herein, means peaks in an X-ray diffractogram, which are caused at certain diffraction angles (Bragg angles) by constructive interference from X-rays scattered by parallel planes of atoms in solid material, which are distributed in an ordered and repetitive pattern in a long-range positional order. Such a solid material is classified as crystalline material, whereas amorphous material is defined as solid material, which lacks long-range order and only displays short-range order, thus resulting in broad scattering. According to literature, long-range order e.g. extends over approximately 100 to 1000 atoms, whereas short-range order is over a few atoms only (see "Fundamentals of Powder Diffraction and Structural Characterization of Materials" by Vitalij K. Pecharsky and Peter Y. Zavalij, Kluwer Academic Publishers, 2003, page 3).

The term "essentially the same" with reference to powder X-ray diffraction means that variabilities in reflection positions and relative intensities of the reflections are to be taken into account. For example, a typical precision of the 2-Theta values is in the range of ±0.2° 2-Theta, preferably in the range of ±0.1° 2-Theta. Thus, a reflection that usually appears at 15.3° 2-Theta for example can appear between 15.1° and 15.5° 2-Theta, preferably between 15.2° and 15.4° 2-Theta on most X-ray diffractometers under standard conditions. Furthermore, one skilled in the art will appreciate that relative reflection intensities will show inter-apparatus variability as well as variability due to degree of crystallinity, preferred orientation, sample preparation and other factors known to those skilled in the art and should be taken as qualitative measure only.

The term "solid state form" as used herein refers to any crystalline and/or amorphous phase of a compound. Crystalline phases include anhydrous/non-solvated forms of a compound and their polymorphs, hydrates and solvates of a compound and their polymorphs, salts and co-crystals of a compound and any mixtures thereof.

The terms "anhydrous" or "anhydrate" as used herein refer to a crystalline solid where no water is cooperated in or accommodated by the crystal structure. Anhydrous forms may still contain residual water, which is not part of the crystal structure but may be adsorbed on the surface or absorbed in disordered regions of the crystal. Typically, an anhydrous form does not contain more than 1.0 weight %, preferably not more than 0.5 weight %, based on the weight of the crystalline form. The water content can be determined by Karl-Fischer Coulometry and/or by thermogravimetric analysis (TGA), e.g. by determining the mass loss in the range of from 25 to 180° C. or 190° C. at a heating rate of 10 K/min.

The term "non-solvated" as used herein, when talking about a crystalline solid indicates that no organic solvent is cooperated in or accommodated by the crystal structure. Non-solvated forms may still contain residual organic solvents, which are not part of the crystal structure but may be adsorbed on the surface or absorbed in disordered regions of the crystal. Typically, a non-solvated form does not contain more than 1.0 weight %, preferably not more than 0.5 weight % of organic solvents, based on the weight of the crystalline form. The organic solvent content can be determined by thermogravimetric analysis (TGA), e.g. by determining the mass loss in the range of from 25 to 180° C. or 190° C. at a heating rate of 10 K/min or by $^1$H-NMR.

The term "hydrate" as used herein, refers to a crystalline solid where either water is cooperated in or accommodated by the crystal structure e.g. is part of the crystal structure or entrapped into the crystal (water inclusions). Thereby, water can be present in a stoichiometric or non-stoichiometric amount. When water is present in stoichiometric amount, the hydrate may be referred to by adding greek numeral prefixes. For example, a hydrate may be referred to as a hemihydrate or as a monohydrate depending on the water/compound stoichiometry. The water content can be measured, for example, by Karl-Fischer-Coulometry.

The terms "dehydrating" or "dehydration" as used herein, describe the at least partial removal of water from the crystal structure of the host molecule.

Crystalline avapritinib according to the present invention may be referred to herein as being characterized by a powder X-ray diffractogram "as shown in" a figure. The person skilled in the art understands that factors such as variations in instrument type, response and variations in sample directionality, sample concentration, sample purity, sample history and sample preparation may lead to variations, for example relating to the exact reflection or peak positions and intensities. However, a comparison of the graphical data in the figures herein with the graphical data generated for an unknown physical form and the confirmation that two sets of graphical data relate to the same crystal form is well within the knowledge of a person skilled in the art.

As used herein, the term "mother liquor" refers to the solution remaining after crystallization of a solid from said solution.

A "predetermined amount" as used herein with regard to crystalline avapritinib (e.g. Form A or Form B or Form Hy1) of the present invention refers to the initial amount of the crystalline avapritinib used for the preparation of a pharmaceutical composition having a desired dosage strength of avapritinib.

As used herein, the term "effective amount" in conjunction with the crystalline avapritinib (e.g. Form A or Form B or Form Hy1) of the present invention encompasses an amount of the crystalline avapritinib which causes the desired therapeutic or prophylactic effect.

As used herein, the term "about" means within a statistically meaningful range of a value. Such a range can be within an order of magnitude, typically within 10%, more typically within 5%, even more typically within 1% and most typically within 0.1% of the indicated value or range.

Sometimes, such a range can lie within the experimental error, typical of standard methods used for the measurement and/or determination of a given value or range.

The term "pharmaceutically acceptable excipient" as used herein refers to substances, which do not show a significant pharmacological activity at the given dose and that are added to a pharmaceutical composition in addition to the active pharmaceutical ingredient. Excipients may take the function of vehicle, diluent, release agent, disintegrating agent, dissolution modifying agent, absorption enhancer, stabilizer or a manufacturing aid among others. Excipients may include fillers (diluents), binders, disintegrants, lubricants and glidants.

The terms "filler" or "diluent" as used herein refer to substances that are used to dilute the active pharmaceutical ingredient prior to delivery. Diluents and fillers can also serve as stabilizers.

As used herein the term "binder" refers to substances which bind the active pharmaceutical ingredient and pharmaceutically acceptable excipient together to maintain cohesive and discrete portions.

The terms "disintegrant" or "disintegrating agent" as used herein refer to substances which, upon addition to a solid pharmaceutical composition, facilitate its break-up or disintegration after administration and permits the release of the active pharmaceutical ingredient as efficiently as possible to allow for its rapid dissolution.

The term "lubricant" as used herein refers to substances which are added to a powder blend to prevent the compacted powder mass from sticking to the equipment during tableting or encapsulation process. They aid the ejection of the tablet from the dies and can improve powder flow.

The term "glidant" as used herein refers to substances which are used for tablet and capsule formulations in order to improve flow properties during tablet compression and to produce an anti-caking effect.

DETAILED DESCRIPTION OF THE INVENTION

Figure 1:
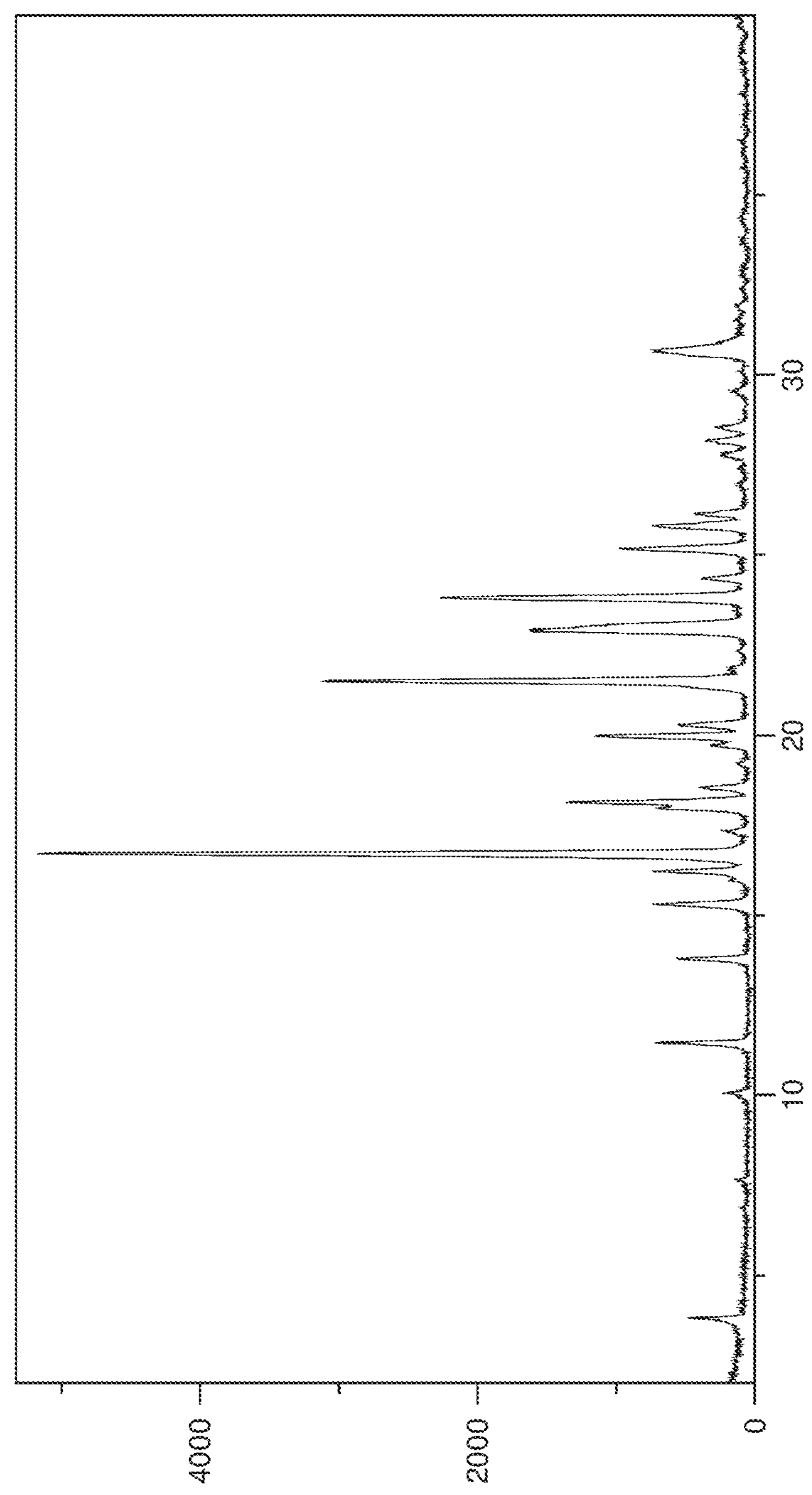
FIG. 1: illustrates a representative PXRD of crystalline avapritinib Form A according to the present invention. The x-axis shows the scattering angle in °2-Theta, the y-axis shows the intensity of the scattered X-ray beam in counts of detected photons.

In a first aspect the present invention relates to avapritinib according to the chemical structure as depicted in Formula (I)

Formula (I)

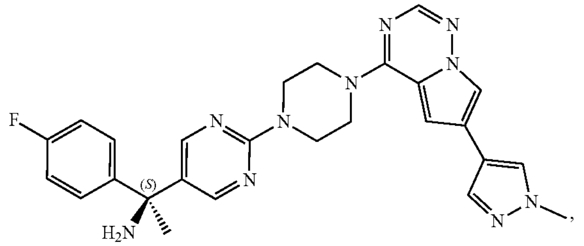

characterized in that said avapritinib is crystalline.

Preferably, crystalline avapritinib of the present invention is characterized as being anhydrous, more preferably as being non-solvated.

In particular, the present invention concerns different crystalline forms of avapritinib, e.g. polymorphs of avapritinib hereinafter also designated as "Form A" and "Form B".

Form A and Form B of avapritinib of the present invention may be characterized by analytical methods well known in the field of the pharmaceutical industry for characterizing crystalline solids. Such methods comprise but are not limited to powder X-ray diffraction, single crystal X-ray diffraction, FTIR, DSC, TGA and GMS. The crystalline forms of the present invention may be characterized by one of the aforementioned analytical methods or by combining two or more of them. In particular, they may be characterized by any one of the following embodiments or by combining two or more of the following embodiments.

Avapritinib Form A, Composition Comprising Form A and Process for Preparing the Same In one embodiment, the invention relates to crystalline avapritinib (Form A) characterized by having a PXRD comprising reflections at 2-Theta angles of:

(15.3±0.2)°, (16.7±0.2)° and (21.5±0.2)°; or
(3.8±0.2)°, (15.3±0.2)°, (16.7±0.2)° and (21.5±0.2)°; or
(3.8±0.2)°, (11.5±0.2)°, (15.3±0.2)°, (16.7±0.2)° and (21.5±0.2)°; or
(3.8±0.2)°, (11.5±0.2)°, (15.3±0.2)°, (16.7±0.2)°, (21.5±0.2)° and (23.8±0.2)°; or
(3.8±0.2)°, (11.5±0.2)°, (15.3±0.2)°, (16.7±0.2)°, (18.1±0.2)°, (21.5±0.2)° and (23.8±0.2)°; or
(3.8±0.2)°, (11.5±0.2)°, (15.3±0.2)°, (16.7±0.2)°, (18.1±0.2)°, (20.0±0.2)°, (21.5±0.2)° and (23.8±0.2)°; or
(3.8±0.2)°, (11.5±0.2)°, (13.8±0.2)°, (15.3±0.2)°, (16.7±0.2)°, (18.1±0.2)°, (20.0±0.2)°, (21.5±0.2)° and (23.8±0.2)°; or
(3.8±0.2)°, (11.5±0.2)°, (13.8±0.2)°, (15.3±0.2)°, (16.2±0.2)°, (16.7±0.2)°, (18.1±0.2)°, (20.0±0.2)°, (21.5±0.2)° and (23.8±0.2)°, when measured at RT with Cu-Kalpha$_{1,2}$ radiation having a wavelength of 0.15419 nm.

In a further embodiment the invention relates to crystalline avapritinib (Form A) characterized by having a PXRD comprising reflections at 2-Theta angles of:

(15.3±0.1)°, (16.7±0.1)° and (21.5±0.1)°; or
(3.8±0.1)°, (15.3±0.1)°, (16.7±0.1)° and (21.5±0.1)°; or
(3.8±0.1)°, (11.5±0.1)°, (15.3±0.1)°, (16.7±0.1)° and (21.5±0.1)°; or (3.8±0.1)°, (11.5±0.1)°, (15.3±0.1)°, (16.7±0.1)°, (21.5±0.1)° and (23.8±0.1)°; or
(3.8±0.1)°, (11.5±0.1)°, (15.3±0.1)°, (16.7±0.1)°, (18.1±0.1)°, (21.5±0.1)° and (23.8±0.1)°; or
(3.8±0.1), (11.5±0.1), (15.3±0.1), (16.7±0.1), (18.1±0.1), (20.0±0.1), (21.5±0.1)° and (23.8±0.1)°; or
(3.8±0.1)°, (11.5±0.1)°, (13.8±0.1)°, (15.3±0.1)°, (16.7±0.1)°, (18.1±0.1)°, (20.0±0.1)°, (21.5±0.1)° and (23.8±0.1)°; or
(3.8±0.1)°, (11.5±0.1)°, (13.8±0.1)°, (15.3±0.1)°, (16.2±0.1)°, (16.7±0.1)°, (18.1±0.1)°, (20.0±0.1)°, (21.5±0.1)° and (23.8±0.1)°, when measured at a temperature in the range of from 20 to 30° C. with Cu-Kalpha$_{1,2}$ radiation having a wavelength of 0.15419 nm.

In another embodiment the invention relates to crystalline avapritinib (Form A) characterized by having a PXRD essentially the same as shown in FIG. 1, when measured at RT with Cu-Kalpha$_{1,2}$ radiation having a wavelength of 0.15419 nm.

In another embodiment, the present invention relates to crystalline avapritinib (Form A), characterized by having a DSC curve comprising an endothermic peak, preferably a single endothermic peak, having a peak onset at a temperature of (192±5)° C., preferably of (192±3)° C., more preferably of (192±1)° C., when measured at a heating rate of 10 K/min.

In a further embodiment, the present invention relates to crystalline avapritinib (Form A), characterized by having a DSC curve comprising an endothermic peak, preferably a single endothermic peak, having a peak maximum at a temperature of (193±5)° C., preferably of (193±3)° C., more preferably of (193±1)° C., when measured at a heating rate of 10 K/min.

In another embodiment, the present invention relates to crystalline avapritinib (Form A), characterized by having a TGA curve showing a mass loss of not more than 0.5 weight %, preferably of not more than 0.3 weight % based on the weight of the crystalline avapritinib, when heated from 25 to 180° C. at a rate of 10 K/min.

In yet another embodiment, the present invention relates to crystalline avapritinib (Form A) characterized by exhibiting a monoclinic unit cell having space group 12 with the following parameters:

| | |
|---|---|
| a = 17.799 (3) Å | alpha = 90° |
| b = 5.7409 (13) Å | beta = 99.338 (18)° |
| c = 47.072 (10) Å | gamma = 90° |

when measured with single crystal X-ray diffraction at (193±2) K with Mo-Kalpha$_{1,2}$ radiation having a wavelength of 0.71073 Angstrom.

In a further embodiment, the present invention relates to crystalline avapritinib (Form A) characterized by showing a mass change of less than 0.2 w-%, based on the weight of the crystalline form, when measured with GMS at a relative humidity in the range of from 0 to 90% and a temperature of (25.0±1.0)° C.

In one embodiment, the present invention relates to crystalline avapritinib (Form A) characterized as being anhydrous.

In another embodiment, the present invention relates to crystalline avapritinib (Form A) characterized as being non-solvated.

In a further embodiment, the present invention relates to crystalline avapritinib (Form A) characterized as being non-hygroscopic.

In another aspect, the present invention relates to a composition comprising crystalline avapritinib (Form A) of the present invention as defined in any of the embodiments described above, said composition being essentially free of any other solid state form of avapritinib. For example, a composition comprising crystalline Form A of avapritinib of the present invention comprises at most 20 weight %, preferably at most 10 w-%, more preferably at most 5 w-%, 4 w-%, 3 w-%, 2 w-% or 1 w-% of any other solid state form of avapritinib, based on the weight of the composition. Preferably, the any other solid state form is crystalline Form B of avapritinib according to the present invention or amorphous avapritinib.

Form B of avapritinib exhibits a PXRD comprising amongst others characteristic reflections at 2-Theta angles of (7.1±0.2)°, (12.2±0.2)° and (14.6±0.2)°, when measured at a temperature in the range of from 20 to 30° C. with Cu-Kalpha$_{1,2}$ radiation having a wavelength of 0.15419 nm. Therefore, the absence of reflections at 2-Theta angles of (7.1±0.2)°, (12.2±0.2)° and (14.6±0.2)°, in the PXRD confirms the absence of form B of avapritinib in the composition.

Hence, in a preferred embodiment, the present invention relates to a composition comprising the crystalline avapritinib (Form A) of the present invention as defined in any one of the embodiments described above, said composition having a PXRD comprising no reflections at 2-Theta angles of (7.1±0.2)°, (12.2±0.2)° and (14.6±0.2)°, when measured at a temperature in the range of from 20 to 30° C. with Cu-Kalpha$_{1,2}$ radiation having a wavelength of 0.15419 nm.

In another embodiment, the invention relates to a composition comprising at least 90 w-%, including at least 90, 91, 92, 93, 94, 95, 96, 97, 98 and 99 w-%, and also including equal to about 100 w-% of the crystalline Form A of avapritinib as defined in any one of the embodiments described above, based on the total weight of the composition. The remaining material may comprise other solid-state form(s) of avapritinib, and/or reaction impurities and/or processing impurities arising from the preparation of the composition.

In a further aspect, the present invention relates to a process for the preparation of crystalline avapritinib (Form A) or the composition comprising crystalline avapritinib (Form A) as defined in any one of the aspects and their corresponding embodiments described above comprising:

(a) dissolving avapritinib in a suitable solvent or solvent mixture under heating;
(b) optionally filtering the solution obtained in (a);
(c) cooling the solution provided in (a) or (b) in order to initiate crystallization;
(d) optionally, adding seed crystals of crystalline avapritinib (Form A) according to the present invention to the mixture of (c);
(e) separating at least a part of the crystals obtained in (c) or (d) from the mother liquor;
(f) optionally, washing the isolated crystals obtained in (e); and
(g) drying the crystals obtained in (e) or (f).

Avapritinib can for example be prepared according to the procedure provided in example 7 of WO 2015/057873 A1.

In a first step, avapritinib is dissolved in a suitable solvent or solvent mixture. The suitable solvent or solvent mixture may be selected from the group consisting of alcohols, ketones, halogenated hydrocarbons, aromatic hydrocarbons, esters and ethers or any mixtures thereof. For example, the suitable solvent or solvent mixture may be selected from the group consisting of ethanol, 1-propanol, 2-propanol, n-butanol, 2-butanol, acetone, methyl ethyl ketone, methyl isobutyl ketone, cyclohexanone, dichloromethane, chloroform, methyl acetate, ethyl acetate, isopropyl acetate, n-butyl acetate, isobutyl acetate, 2-methyltetrahydrofuran, cylopropyl methyl ether, anisole, toluene and xylene (isomers) or any mixtures thereof. The suitable solvent may be further selected from the group consisting of mesitylene, chlorobenzene, nitromethane, dimethyl formamide and dimethoxysulfoxide or any mixtures thereof.

In step (a) avapritinib is applied at a concentration in the range of from about 10 to 50 g/L solvent or solvent mixture, preferably of from about 25 to 50 g/L solvent or solvent mixture. Avapritinib is dissolved in the solvent or solvent mixture under heating, e.g. heating to reflux temperature of the solvent or solvent mixture.

Optionally the hot solution may be filtrated in order to remove any possible undissolved particles.

The obtained clear solution is then cooled to room temperature in order to initiate crystallization. The cooling rate is thereby not critical and may range from about (−0.1) to (−5)K/min, e.g. the cooling rate is about (−1)K/min or (−2)K/min. In one embodiment the solution is allowed to cool naturally to room temperature. In addition, the solution may be cooled further to a temperature in the range of from about (−10) to 10° C. in order to increase the yield.

Optionally, avapritinib form A seed crystals, which may be prepared according to example 1 herein, may be added in order to promote crystallization and/or to control particle size distribution. The amount of seed crystals employed may range from about 1 to 20 weight %, preferably from about 1 to 10 weight % and most preferably from about 1 to 5 weight %, based on the weight of applied avapritinib starting material.

Once crystalline form A of avapritinib of the present invention is obtained or preferably obtained in essentially pure form, at least a part of the crystals is separated from the mother liquor. Preferably, the crystals are separated from the mother liquor by any conventional method such as filtration, centrifugation, solvent evaporation or decantation, more preferably by filtration or centrifugation and most preferably by filtration.

Optionally, in a further step the isolated crystals are washed with a suitable solvent or solvent mixture. The suitable solvent or solvent mixture may be selected from the group consisting of alcohols, ketones, halogenated hydrocarbons, aromatic hydrocarbons, esters and ethers or any mixtures thereof. For example, the suitable solvent or solvent mixture may be selected from the group consisting of ethanol, 1-propanol, 2-propanol, n-butanol, 2-butanol, acetone, methyl ethyl ketone, methyl isobutyl ketone, cyclohexanone, dichloromethane, chloroform, methyl acetate, ethyl acetate, isopropyl acetate, n-butyl acetate, isobutyl acetate, 2-methyltetrahydrofuran, cylopropyl methyl ether, anisole, toluene, xylene (isomers) or any mixtures thereof. Further mesitylene, chlorobenzene, nitromethane, dimethyl formamide and dimethoxysulfoxide or any mixtures thereof. The suitable solvent may be further selected from the group consisting of mesitylene, chlorobenzene, nitromethane, dimethyl formamide and dimethoxysulfoxide or any mixtures thereof.

The obtained crystals may then optionally be dried. Drying may be performed at a temperature in the range of from about 20 to 80° C., preferably in the range of from about 20 to 40° C. and most preferably drying is performed at about RT. Drying may be performed for a period in the range of from about 1 to 72 hours, preferably of from about 2 to 48 hours, more preferably of from about 4 to 24 hours and most preferably of from about 6 to 18 hours. Drying may be performed at ambient pressure and/or under reduced pressure. Preferably, drying is performed at reduced pressure of about 100 mbar or less, more preferably of about 50 mbar or less, for example a vacuum of about 35 mbar is applied for drying.

Avapritinib Form B, Composition Comprising Form B and Process for Preparing the Same In one embodiment, the invention relates to a crystalline form of avapritinib (Form B) characterized by having a PXRD comprising reflections at 2-Theta angles of:

(3.6±0.2)°, (16.0±0.2)° and (14.6±0.2)°; or
(3.6±0.2)°, (12.2±0.2)°, (14.6±0.2)° and (16.0±0.2)°; or
(3.6±0.2)°, (7.1±0.2)°, (12.2±0.2)°, (14.6±0.2)° and (16.0±0.2)°; or
(3.6±0.2)°, (7.1±0.2)°, (12.2±0.2)°, (14.6±0.2)°, (16.0±0.2)° and (18.9±0.2)°; or
(3.6±0.2)°, (7.1±0.2)°, (12.2±0.2)°, (14.6±0.2)°, (16.0±0.2)°, (18.9±0.2)° and (20.3±0.2)°; or
(3.6±0.2)°, (7.1±0.2)°, (11.3±0.2)°, (12.2±0.2)°, (14.6±0.2)°, (16.0±0.2)°, (18.9±0.2)° and (20.3±0.2)°; or
(3.6±0.2)°, (7.1±0.2)°, (10.1±0.2)°, (11.3±0.2)°, (12.2±0.2)°, (14.6±0.2)°, (16.0±0.2)°, (18.9±0.2)° and (20.3±0.2)°; or
(3.6±0.2)°, (7.1±0.2)°, (10.1±0.2)°, (11.3±0.2)°, (12.2±0.2)°, (14.6±0.2)°, (16.0±0.2)°, (18.9±0.2)°, (20.3±0.2)° and (22.7±0.2)°, when measured at RT with Cu-Kalpha$_{1,2}$ radiation having a wavelength of 0.15419 nm.

In a further embodiment the invention relates to a crystalline form of avapritinib (Form B) characterized by having a PXRD comprising reflections at 2-Theta angles of:

(3.6±0.1)°, (16.0±0.1)° and (14.6±0.1)°; or
(3.6±0.1)°, (12.2±0.1)°, (14.6±0.1)° and (16.0±0.1)°; or
(3.6±0.1)°, (7.1±0.1)°, (12.2±0.1)°, (14.6±0.1)° and (16.0±0.1)°; or
(3.6±0.1)°, (7.1±0.1)°, (12.2±0.1)°, (14.6±0.1)°, (16.0±0.1)° and (18.9±0.1)°; or
(3.6±0.1)°, (7.1±0.1)°, (12.2±0.1)°, (14.6±0.1)°, (16.0±0.1)°, (18.9±0.1)° and (20.3±0.1)°; or
(3.6±0.1)°, (7.1±0.1)°, (11.3±0.1)°, (12.2±0.1)°, (14.6±0.1)°, (16.0±0.1)°, (18.9±0.1)° and (20.3±0.1)°; or
(3.6±0.1)°, (7.1±0.1)°, (10.1±0.1)°, (11.3±0.1)°, (12.2±0.1)°, (14.6±0.1)°, (16.0±0.1)°, (18.9±0.1)° and (20.3±0.1)°; or
(3.6±0.1)°, (7.1±0.1)°, (10.1±0.1)°, (11.3±0.1)°, (12.2±0.1)°, (14.6±0.1)°, (16.0±0.1)°, (18.9±0.1)°, (20.3±0.1)° and (22.7±0.1)°, when measured at a temperature in the range of from 20 to 30° C. with Cu-Kalpha$_{1,2}$ radiation having a wavelength of 0.15419 nm.

Figure 6:
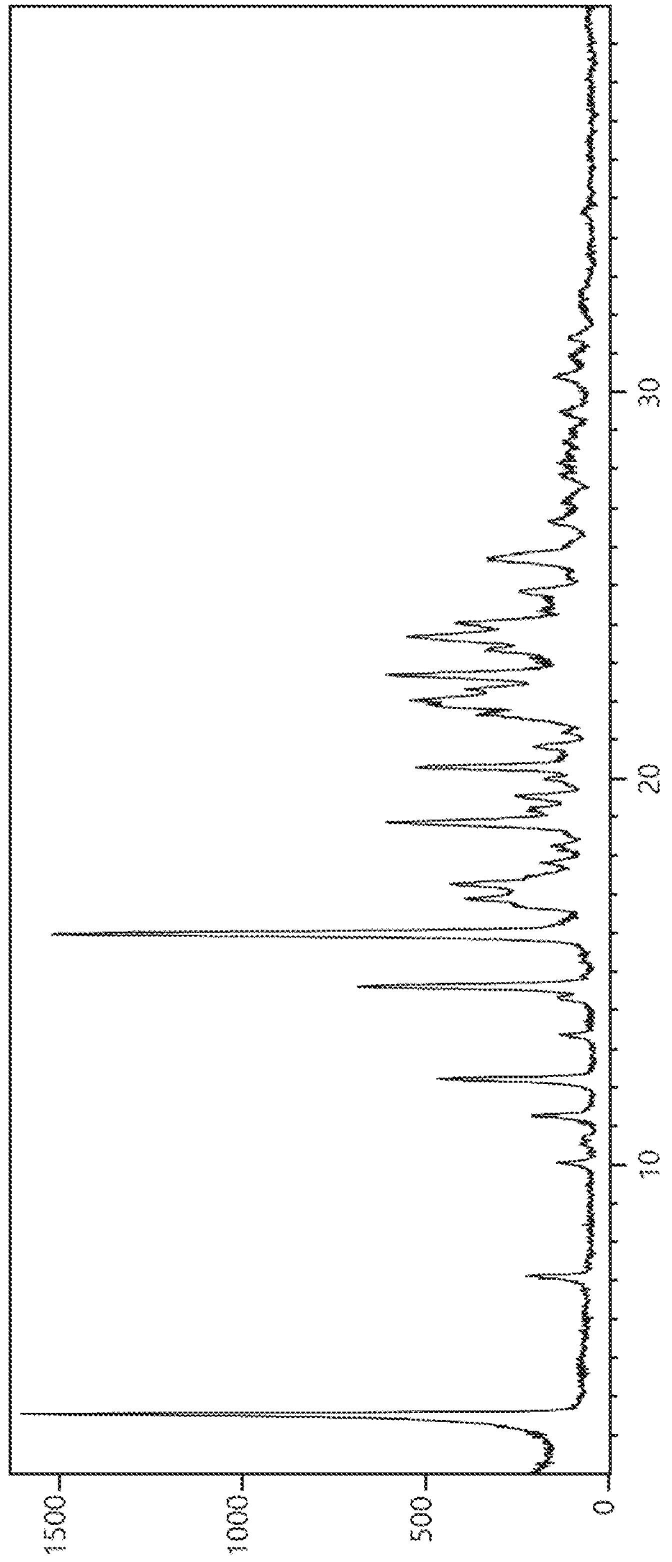
FIG. 6: illustrates a representative PXRD of crystalline avapritinib Form B according to the present invention. The x-axis shows the scattering angle in °2-Theta, the y-axis shows the intensity of the scattered X-ray beam in counts of detected photons.

In another embodiment the invention relates to a crystalline form of avapritinib (Form B) characterized by having a PXRD essentially the same as shown in FIG. 6, when measured at RT with Cu-Kalpha$_{1,2}$ radiation having a wavelength of 0.15419 nm.

In another embodiment, the present invention relates to crystalline avapritinib (Form B), characterized by having a DSC curve comprising an endothermic peak, having a peak onset at a temperature of (180±5)° C., preferably of (180±3)° C., more preferably of (180±1)° C., when measured at a heating rate of 10 K/min.

In a further embodiment, the present invention relates to crystalline avapritinib (Form B), characterized by having a DSC curve comprising an endothermic peak, preferably a single endothermic peak, having a peak maximum at a temperature of (182±5)° C., preferably of (182±3)° C., more preferably of (182±1)° C., when measured at a heating rate of 10 K/min.

In another embodiment, the present invention relates to crystalline avapritinib (Form B), characterized by having a TGA curve showing a mass loss of not more than 0.5 weight %, preferably of not more than 0.4 weight %, based on the weight of the crystalline avapritinib, when heated from 25 to 180° C. at a rate of 10 K/min.

In a further embodiment, the present invention relates to crystalline avapritinib (Form B) characterized by showing a mass change of less than 0.5 w-%, based on the weight of the crystalline form, when measured with GMS at a relative humidity in the range of from 0 to 90% and a temperature of (25.0±1.0)° C.

In one embodiment, the present invention relates to crystalline avapritinib (Form B) characterized as being anhydrous.

In another embodiment, the present invention relates to crystalline avapritinib (Form B) characterized as being non-solvated.

In a further embodiment, the present invention relates to crystalline avapritinib (Form B) characterized as being slightly hygroscopic.

In another aspect, the present invention relates to a composition comprising crystalline avapritinib (Form B) of the present invention as defined in any of the embodiments described above, said composition being essentially free of any other solid state form of avapritinib. For example, a composition comprising crystalline Form B of avapritinib of the present invention comprises at most 20 weight %, preferably at most 10 w-%, more preferably at most 5 w-%, 4 w-%, 3 w-%, 2 w-% or 1 w-% of any other solid state form of avapritinib, based on the weight of the composition.

Preferably, the any other solid state form is crystalline Form A of avapritinib according to the present invention or amorphous avapritinib.

Form A of avapritinib exhibits a PXRD comprising a characteristic reflection at (15.3±0.2)° 2-Theta, when measured at a temperature in the range of from 20 to 30° C. with Cu-Kalpha$_{1,2}$ radiation having a wavelength of 0.15419 nm. Therefore, the absence of reflections at 2-Theta angles of (15.3±0.2)° in the PXRD confirms the absence of Form A of avapritinib in the composition.

Hence, in a preferred embodiment, the present invention relates to a composition comprising the crystalline avapritinib (Form B) of the present invention as defined in any one of the embodiments described above, said composition having a PXRD comprising no reflections at 2-Theta angles of (15.3±0.2)°, when measured at a temperature in the range of from 20 to 30° C. with Cu-Kalpha$_{1,2}$ radiation having a wavelength of 0.15419 nm.

In another embodiment, the invention relates to a composition comprising at least 90 w-%, including at least 90, 91, 92, 93, 94, 95, 96, 97, 98 and 99 w-%, and also including equal to about 100 w-% of the crystalline Form B of avapritinib as defined in any one of the embodiments described above, based on the total weight of the composition. The remaining material may comprise other solid form(s) of avapritinib, and/or reaction impurities and/or processing impurities arising from the preparation of the composition.

In a further aspect, the present invention relates to a process for the preparation of crystalline avapritinib (Form B) or the composition comprising crystalline avapritinib (Form B) as defined in any one of the aspects and their corresponding embodiments described above comprising:

(a) dissolving avapritinib in a solvent comprising isopentanol under heating;
(b) optionally filtering the solution obtained in (a);
(c) cooling the solution provided in (a) or (b) in order to initiate crystallization;
(d) optionally, adding seed crystals of crystalline avapritinib (Form B) according to the present invention to the mixture of (c);
(e) separating at least a part of the crystals obtained in (c) or (d) from the mother liquor;
(f) optionally, washing the isolated crystals obtained in (e); and
(g) drying the crystals obtained in (e) or (f).

Avapritinib can for example be prepared according to the procedure provided in example 7 of WO 2015/057873 A1.

In a first step, avapritinib is dissolved in a solvent comprising isopentanol, preferably the solvent consists of isopentanol.

In step (a) avapritinib is applied at a concentration in the range of from about 30 to 45 g/L solvent, preferably the avapritinib concentration is about 35 g/L solvent. Avapritinib is dissolved in the solvent or solvent mixture under heating, e.g. heating to reflux temperature of the solvent.

Optionally the hot solution may be filtrated in order to remove any possible undissolved particles.

The obtained clear solution is then cooled to room temperature in order to initiate crystallization. The cooling rate is thereby not critical and may range from about (−0.1) to (−5)K/min, e.g. the cooling rate is about (−1)K/min or (−3)K/min. In one embodiment the solution is allowed to cool naturally to room temperature. In addition, the solution may be cooled further to a temperature in the range of from about (−10) to 10° C. in order to increase the yield.

Optionally, avapritinib form B seed crystals, which may be prepared according to example 2 herein, may be added in order to promote crystallization and/or to control particle size distribution. The amount of seed crystals employed may range from about 1 to 20 weight %, preferably from about 1 to 10 weight % and most preferably from about 1 to 5 weight %, based on the weight of applied avapritinib starting material.

Once crystalline form B of avapritinib of the present invention is obtained or preferably obtained in essentially pure form, at least a part of the crystals is separated from the mother liquor. Preferably, the crystals are separated from the mother liquor by any conventional method such as filtration, centrifugation, solvent evaporation or decantation, more preferably by filtration or centrifugation and most preferably by filtration.

Optionally, in a further step the isolated crystals are washed with a suitable solvent or solvent mixture. The suitable solvent or solvent mixture preferably comprises isopentanol, more preferably the solvent consists of isopentanol.

The obtained crystals may then optionally be dried. Drying may be performed at a temperature in the range of from about 20 to 80° C., preferably in the range of from about 20 to 40° C. and most preferably drying is performed at about RT. Drying may be performed for a period in the range of from about 1 to 72 hours, preferably of from about 2 to 48 hours, more preferably of from about 4 to 24 hours and most preferably of from about 6 to 18 hours. Drying may be performed at ambient pressure and/or under reduced pressure. Preferably, drying is performed at reduced pressure of about 100 mbar or less, more preferably of about 50 mbar or less, for example a vacuum of about 35 mbar is applied for drying.

In another aspect the present invention relates to a hydrate of avapritinib according to the chemical structure as depicted in Formula (II)

Formula (II)

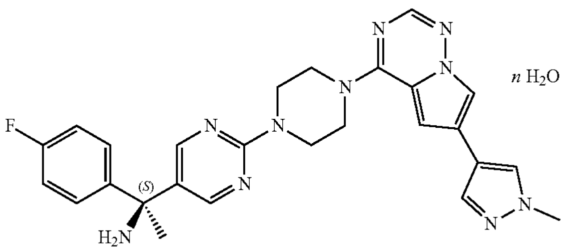

, wherein n is in the range of from 0.8 to 1.2, preferably of from 0.9 to 1.1, more preferably of from 0.95 to 1.05 and most preferably n is 1.0.

In particular, the present invention concerns a hydrate of avapritinib, hereinafter also designated as "Form Hy1".

Form Hy1 of avapritinib of the present invention may be characterized by analytical methods well known in the field of the pharmaceutical industry for characterizing crystalline solids. Such methods comprise but are not limited to powder X-ray diffraction, FTIR, DSC, TGA and GMS. The hydrate Form Hy1 of the present invention may be characterized by one of the aforementioned analytical methods or by combining two or more of them. In particular, Form Hy1 may be characterized by any one of the following embodiments or by combining two or more of the following embodiments.

Avapritinib Hydrate Form Hy1, Composition Comprising Hydrate Form Hy1 and Process for Preparing the Same In one embodiment, the invention relates to a hydrate of avapritinib (Form Hy1) characterized by having a PXRD comprising reflections at 2-Theta angles of:

(5.3±0.2)°, (9.3±0.2)° and (10.4±0.2)°; or (5.3±0.2)°, (9.3±0.2)°, (10.4±0.2)° and (13.9±0.2)°; or (5.3±0.2)°, (9.3±0.2)°, (10.4±0.2)°, (13.9±0.2)° and (25.7±0.2)°; or (5.3±0.2)°, (9.3±0.2)°, (10.4±0.2)°, (12.0±0.2)°, (13.9±0.2)° and (25.7±0.2)°; or (5.3±0.2)°, (9.3±0.2)°, (10.4±0.2)°, (12.0±0.2)°, (13.9±0.2)°, (17.4±0.2)° and (25.7±0.2)°; or (5.3±0.2)°, (9.3±0.2)°, (10.4±0.2)°, (12.0±0.2)°, (13.9±0.2)°, (17.4±0.2)°, (24.7±0.2)° and (25.7±0.2)°; or (5.3±0.2)°, (9.3±0.2)°, (10.4±0.2)°, (12.0±0.2)°, (13.9±0.2)°, (16.1±0.2)°, (17.4±0.2)°, (24.7±0.2)° and (25.7±0.2)°; or (5.3±0.2)°, (9.3±0.2)°, (10.4±0.2)°, (12.0±0.2)°, (13.9±0.2)°, (14.7±0.2)°, (16.1±0.2)°, (17.4±0.2)°, (24.7±0.2)° and (25.7±0.2)°, when measured at a temperature in the range of from 20 to 30° C. with Cu-Kalpha$_{1,2}$ radiation having a wavelength of 0.15419 nm.

In a further embodiment, the invention relates to a hydrate of avapritinib (Form Hy1) characterized by having a PXRD comprising reflections at 2-Theta angles of:

(5.3±0.1)°, (9.3±0.1)° and (10.4±0.1)°; or (5.3±0.1)°, (9.3±0.1)°, (10.4±0.1)° and (13.9±0.1)°; or (5.3±0.1)°, (9.3±0.1)°, (10.4±0.1)°, (13.9±0.1)° and (25.7±0.1)°; or (5.3±0.1)°, (9.3±0.1)°, (10.4±0.1)°, (12.0±0.1)°, (13.9±0.1)° and (25.7±0.1)°; or (5.3±0.1)°, (9.3±0.1)°, (10.4±0.1)°, (12.0±0.1)°, (13.9±0.1)°, (17.4±0.1)° and (25.7±0.1)°; or (5.3±0.1)°, (9.3±0.1)°, (10.4±0.1)°, (12.0±0.1)°, (13.9±0.1)°, (17.4±0.1)°, (24.7±0.1)° and (25.7±0.1)°; or (5.3±0.1)°, (9.3±0.1)°, (10.4±0.1)°, (12.0±0.1)°, (13.9±0.1)°, (16.1±0.1)°, (17.4±0.1)°, (24.7±0.1)° and (25.7±0.1)°; or (5.3±0.1)°, (9.3±0.1)°, (10.4±0.1)°, (12.0±0.1)°, (13.9±0.1)°, (14.7±0.1)°, (16.1±0.1)°, (17.4±0.1)°, (24.7±0.1)° and (25.7±0.1)°, when measured at a temperature in the range of from 20 to 30° C. with Cu-Kalpha$_{1,2}$ radiation having a wavelength of 0.15419 nm.

Figure 11:
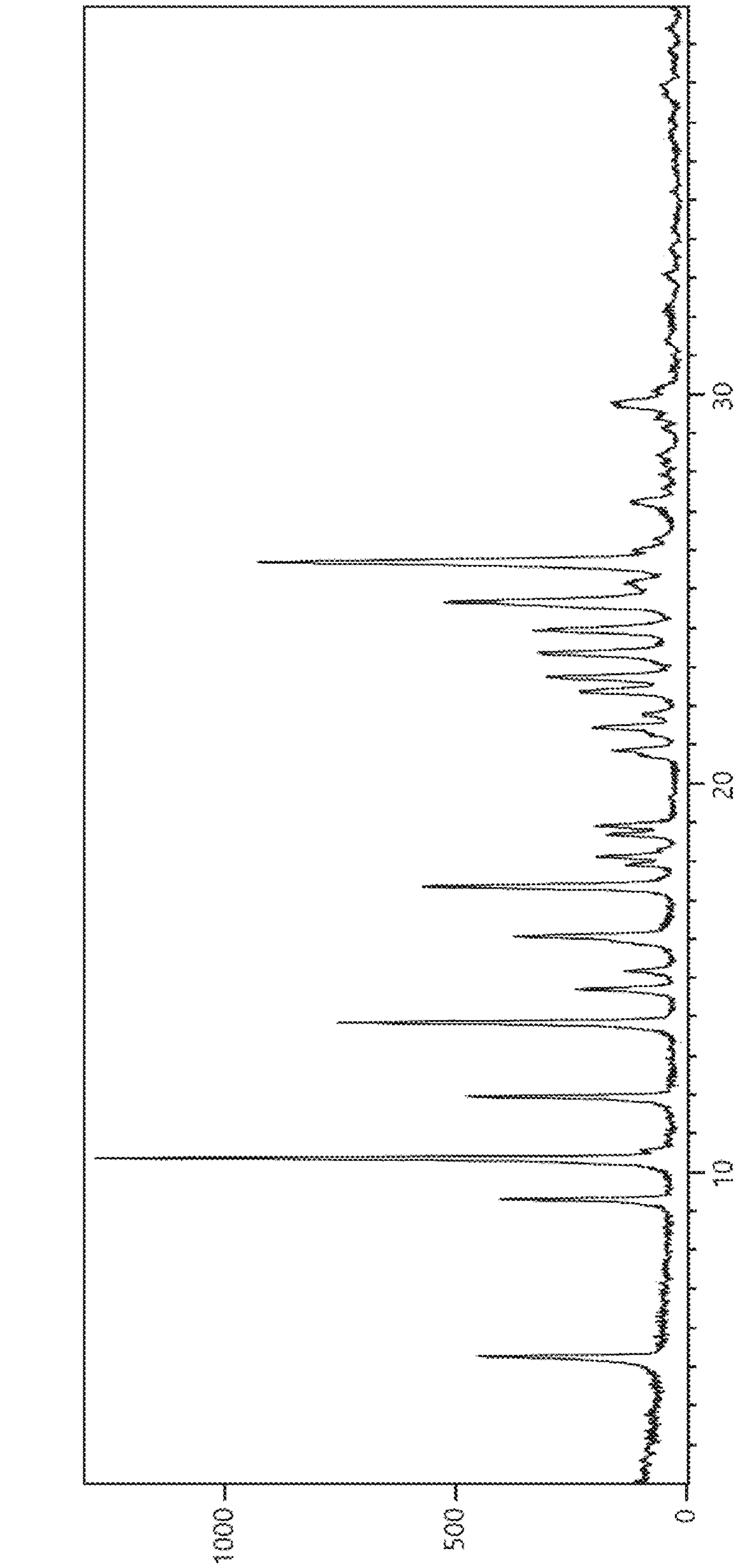
FIG. 11: illustrates a representative PXRD of the avapritinib hydrate Form Hy1 according to the present invention. The x-axis shows the scattering angle in °2-Theta, the y-axis shows the intensity of the scattered X-ray beam in counts of detected photons.

In a further embodiment, the invention relates to a hydrate of avapritinib (Form Hy1) characterized by having a PXRD essentially the same as shown in FIG. 11, when measured at a temperature in the range of from 20 to 30° C. with Cu-Kalpha$_{1,2}$ radiation having a wavelength of 0.15419 nm.

In another embodiment, the present invention relates to a hydrate of avapritinib (Form Hy1) characterized by having an FTIR spectrum comprising peaks at wavenumbers of:

(1584±4) cm$^{-1}$, (1307±4) cm$^{-1}$ and (1123±4) cm$^{-1}$ or;

(1584±4) cm$^{-1}$, (1307±4) cm$^{-1}$, (1123±4) cm$^{-1}$ and (926±4) cm$^{-1}$; or (1584±4) cm$^{-1}$, (1307±4) cm$^{-1}$, (1123±4) cm$^{-1}$, (926±4) cm$^{-1}$ and (762±4) cm$^{-1}$; or (3373±4) cm$^{-1}$, (1584±4) cm$^{-1}$, (1307±4) cm$^{-1}$, (1123±4) cm$^{-1}$, (926±4) cm$^{-1}$ and (762±4) cm$^{-1}$; or (3373±4) cm$^{-1}$, (2981±4) cm$^{-1}$, (1584±4) cm$^{-1}$, (1307±4) cm$^{-1}$, (1123±4) cm$^{-1}$, (926±4) cm$^{-1}$ and (762±4) cm$^{-1}$; or (3373±4) cm$^{-1}$, (2981±4) cm$^{-1}$, (1584±4) cm$^{-1}$, (1491±4) cm$^{-1}$, (1307±4) cm$^{-1}$, (1123±4) cm$^{-1}$, (926±4) cm$^{-1}$ and (762±4) cm$^{-1}$; or (3373±4) cm$^{-1}$, (2981±4) cm$^{-1}$, (1584±4) cm$^{-1}$, (1491±4) cm$^{-1}$, (1426±4) cm$^{-1}$, (1307±4) cm$^{-1}$, (1123±4) cm$^{-1}$, (926±4) cm$^{-1}$ and (762±4) cm$^{-1}$; or (3373±4) cm$^{-1}$, (2981±4) cm$^{-1}$, (1584±4) cm$^{-1}$, (1491±4) cm$^{-1}$, (1426±4) cm$^{-1}$, (1307±4) cm$^{-1}$, (1220±4) cm$^{-1}$, (1123±4) cm$^{-1}$, (926±4) cm$^{-1}$ and (762±4) cm$^{-1}$, when measured at a temperature in the range of from 20 to 30° C. with a diamond ATR cell.

In still another embodiment, the present invention relates to a hydrate of avapritinib (Form Hy1) characterized by having an FTIR spectrum comprising peaks at wavenumbers of:

(1584±2) cm$^{-1}$, (1307±2) cm$^{-1}$ and (1123±2) cm$^{-1}$ or;

(1584±2) cm$^{-1}$, (1307±2) cm$^{-1}$, (1123±2) cm$^{-1}$ and (926±2) cm$^{-1}$; or (1584±2) cm$^{-1}$, (1307±2) cm$^{-1}$, (1123±2) cm$^{-1}$, (926±2) cm$^{-1}$ and (762±2) cm$^{-1}$; or (3373±2) cm$^{-1}$, (1584±2) cm$^{-1}$, (1307±2) cm$^{-1}$, (1123±2) cm$^{-1}$, (926±2) cm$^{-1}$ and (762±2) cm$^{-1}$; or (3373±2) cm$^{-1}$, (2981±2) cm$^{-1}$, (1584±2) cm$^{-1}$, (1307±2) cm$^{-1}$, (1123±2) cm$^{-1}$, (926±2) cm$^{-1}$ and (762±2) cm$^{-1}$; or (3373±2) cm$^{-1}$, (2981±2) cm$^{-1}$, (1584±2) cm$^{-1}$, (1491±2) cm$^{-1}$, (1307±2) cm$^{-1}$, (1123±2) cm$^{-1}$, (926±2) cm$^{-1}$ and (762±2) cm$^{-1}$; or (3373±2) cm$^{-1}$, (2981±2) cm$^{-1}$, (1584±2) cm$^{-1}$, (1491±2) cm$^{-1}$, (1426±2) cm$^{-1}$, (1307±2) cm$^{-1}$, (1123±2) cm$^{-1}$, (926±2) cm$^{-1}$ and (762±2) cm$^{-1}$; or (3373±2) cm$^{-1}$, (2981±2) cm$^{-1}$, (1584±2) cm$^{-1}$, (1491±2) cm$^{-1}$, (1426±2) cm$^{-1}$, (1307±2) cm$^{-1}$, (1220±2) cm$^{-1}$, (1123±2) cm$^{-1}$, (926±2) cm$^{-1}$ and (762±2) cm$^{-1}$, when measured at a temperature in the range of from 20 to 30° C. with a diamond ATR cell.

Figure 12:
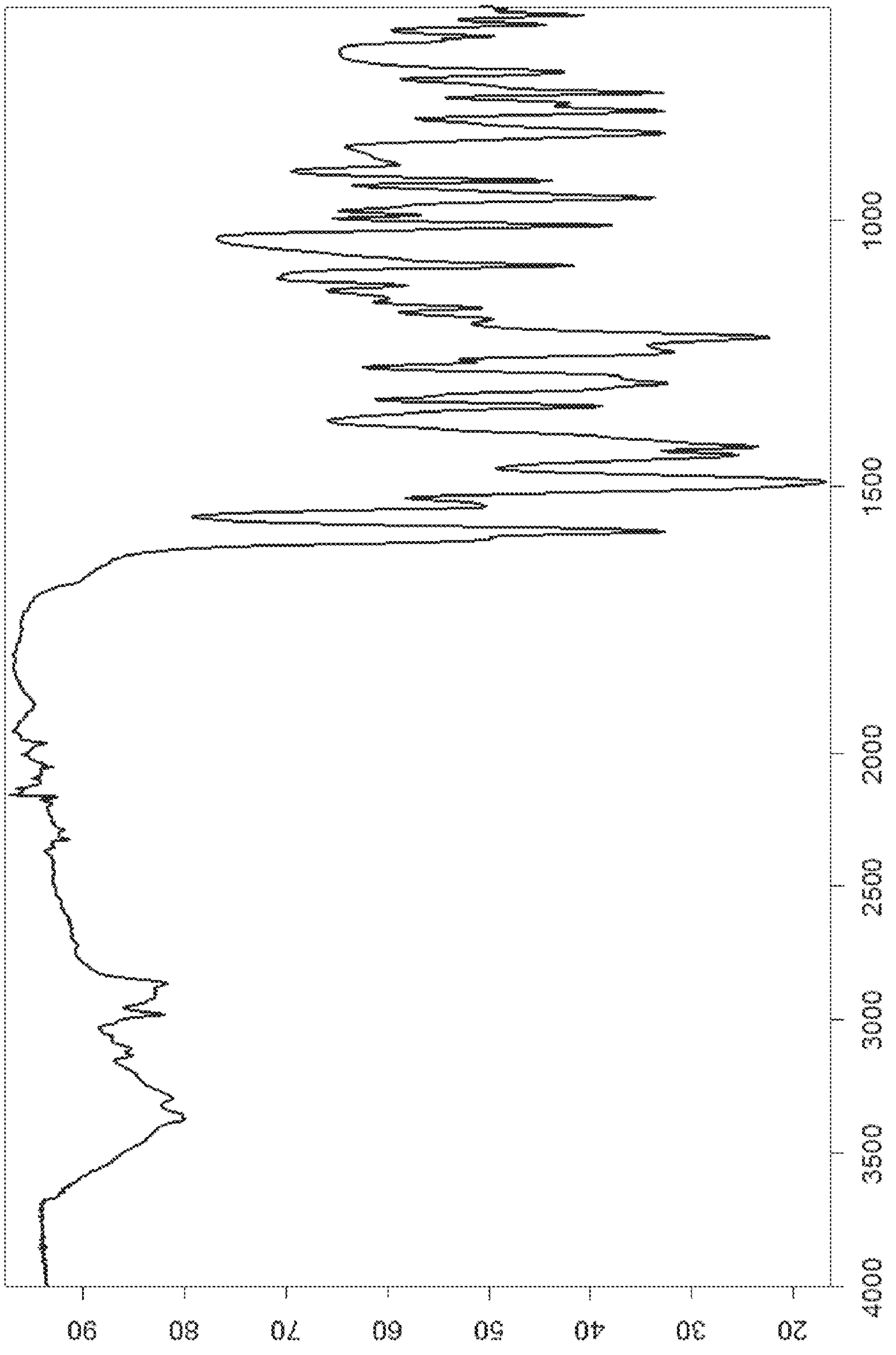
FIG. 12: illustrates a representative FTIR spectrum of the avapritinib hydrate Form Hy1 of the present invention. The x-axis shows the wavenumbers in $cm^{-1}$, the y-axis shows the relative intensity in percent transmittance.

In yet another embodiment, the present invention relates to a hydrate of avapritinib (Form Hy1) characterized by having an FTIR spectrum essentially the same as shown in FIG. 12 of the present invention, when measured at a temperature in the range of from 20 to 30° C. with a diamond ATR cell.

In another embodiment, the present invention relates to a hydrate of avapritinib (Form Hy1), characterized by having a DSC curve comprising an endothermic peak, preferably a first endothermic peak having a peak onset at a temperature of (78±5)° C., preferably of (78±3)° C., more preferably of (78±1)° C., when measured at a heating rate of 10 K/min.

In a further embodiment, the present invention relates to a hydrate of avapritinib (Form Hy1), characterized by having a DSC curve comprising an endothermic peak, preferably a first endothermic peak, having a peak maximum at a temperature of (97±5)° C., preferably of (97±3)° C., more preferably of (97±1)° C., when measured at a heating rate of 10 K/min.

In another embodiment, the present invention relates to a hydrate of avapritinib (Form Hy1), characterized by having a TGA curve showing a mass loss of (3.5±0.2) weight %, preferably of (3.5±0.1) weight %, more preferably of 3.5 weight %, based on the weight of the avapritnib hydrate, when heated from 25 to 110° C. at a rate of 10 K/min.

In a further embodiment, the present invention relates to a hydrate of avapritinib (Form Hy1) characterized by showing a mass change of less than 2.0 w-%, preferably of less than 1.5 w-%, based on the weight of the avapritinib hydrate, when measured with GMS at a relative humidity in the range of from 10 to 90% and a temperature of (25.0±1.0)° C.

In another aspect, the present invention relates to a composition comprising the hydrate of avapritinib (Form Hy1) of the present invention as defined in any of the embodiments described above, said composition being essentially free of any other solid state form of avapritinib. For example, a composition comprising avapritinib Form Hy1 of the present invention comprises at most 20 w-%, preferably at most 10 w-%, more preferably at most 5 w-%, 4 w-%, 3 w-%, 2 w-% or 1 w-% of any other solid state form of avapritinib, based on the weight of the composition. Preferably, the any other solid state form is crystalline Form A of avapritinib according to the present invention or amorphous avapritinib.

Form A of avapritinib exhibits a PXRD comprising amongst others a characteristic reflection at (3.8±0.2)°2-Theta, when measured at a temperature in the range of from 20 to 30° C. with Cu-Kalpha$_{1,2}$ radiation having a wavelength of 0.15419 nm. Therefore, the absence of reflections at 2-Theta angles of (3.8±0.2)° in the PXRD confirms the absence of Form A of avapritinib in the composition.

Hence, in a preferred embodiment, the present invention relates to a composition comprising the hydrate of avapritinib (Form Hy1) of the present invention as defined in any one of the embodiments described above, said composition having a PXRD comprising no reflections at 2-Theta angles of (3.8±0.2)°, when measured at a temperature in the range of from 20 to 30° C. with Cu-Kalpha$_{1,2}$ radiation having a wavelength of 0.15419 nm.

In another embodiment, the invention relates to a composition comprising at least 90 w-%, including at least 90, 91, 92, 93, 94, 95, 96, 97, 98 and 99 w-%, and also including equal to about 100 w-% of the hydrate of avapritinib (Form Hy1) as defined in any one of the embodiments described above, based on the total weight of the composition. The remaining material may comprise other solid form(s) of avapritinib, and/or reaction impurities and/or processing impurities arising from the preparation of the composition.

In a further aspect, the present invention relates to a process for the preparation of the hydrate of avapritinib (Form Hy1) or the composition comprising the hydrate of avapritinib (Form Hy1) as defined in any one of the aspects and their corresponding embodiments described above comprising:

(a) dissolving avapritinib in a solvent comprising water and a water miscible organic solvent under heating;
(b) optionally filtering the solution obtained in (a);
(c) cooling the solution provided in (a) or (b) in order to initiate crystallization;
(d) optionally, adding additional water and/or seed crystals of the crystalline hydrate (Form Hy1) according to the present invention to the mixture of (c);
(e) separating at least a part of the crystals obtained in (c) or (d) from the mother liquor;
(f) optionally, washing the isolated crystals obtained in (e); and
(g) drying the crystals obtained in (e) or (f).

Avapritinib can for example be prepared according to the procedure provided in example 7 of WO 2015/057873 A1.

In a first step, avapritinib is dissolved in a solvent comprising water and a water-miscible organic solvent. The water-miscible organic solvent may be selected from one or more alcohol(s), one or more cyclic ether(s) or any mixtures thereof. The one or more alcohol(s) may be selected from the group consisting of methanol, ethanol and isopropanol or any mixtures thereof. The one or more cyclic ether(s) may be selected from THF, 1,4-dioxane or a mixture thereof. The amount of water-miscible organic solvent of the aqueous solvent mixture provided in step (a) is in the range of from 40 to 90% volume/volume, preferabyl in the range of from 50 to 80% volume/volume and most preferably the amount of water-miscible solvent is about 80% volume/volume. The organic solvent/water ratio shall be selected such, that the avapritinib starting material dissolves upon heating e.g. upon heating to the reflux temperature of the applied solvent. Thereby, avapritinib is applied at a concentration in the range of from about 10 to 100 g/L solvent, preferably in the range of from about 20 to 80 g/L solvent.

Optionally the hot solution may be filtrated in order to remove any possible undissolved particles.

The obtained clear solution is then cooled to a temperture in the range of from about 0 to 5° C. e.g. in an ice-bath in order to initiate crystallization. The cooling rate is thereby not critical and may range from about (−0.1) to (−5)K/min, e.g. the cooling rate is about (−1)K/min or (−3)K/min.

Optionally, avapritinib hydrate Form Hy1 seed crystals, which may be prepared according to any of the methods provided in example 3 herein, may be added in order to promote crystallization and/or to control particle size distribution. The amount of seed crystals employed may range from about 1 to 20 weight %, preferably from about 1 to 10 weight % and most preferably from about 1 to 5 weight %, based on the weight of applied avapritinib starting material. Furthermore, additional water may be added to the mixture in order to initiate crystallization and/or to increase the yield.

Once the hydrate Form Hy1 of avapritinib of the present invention is obtained or preferably obtained in essentially pure form, at least a part of the crystals is separated from the mother liquor. Preferably, the crystals are separated from the mother liquor by any conventional method such as filtration, centrifugation, solvent evaporation or decantation, more preferably by filtration or centrifugation and most preferably by filtration.

Optionally, in a further step the isolated crystals are washed with a suitable solvent or solvent mixture. In one embodiment, water is used as solvent in the washing step.

Finally, the obtained crystals are dried. Drying may be performed at a temperature in the range of from about 20 to 40° C. and most preferably drying is performed at about RT. Drying may be performed for a period in the range of from about 1 to 72 hours, preferably of from about 2 to 48 hours, more preferably of from about 4 to 24 hours and most preferably of from about 6 to 18 hours. Drying may be performed at ambient pressure and/or under reduced pressure. Preferably, drying is performed at reduced pressure of about 100 mbar or less, more preferably of about 50 mbar or less, for example a vacuum of about 35 mbar is applied for drying.

Pharmaceutical Compositions and Medical Use

In a further aspect, the present invention relates to the use of crystalline avapritinib, in particular of crystalline avapritinib Form A or Form B or the composition comprising crystalline avapritinib Form A or Form B, or a hydrate of avapritinib, in particular the hydrate Form Hy1 or the composition comprising the hydrate Form Hy1 as defined in any one of the aspects and their corresponding embodiments described above for the preparation of a pharmaceutical composition.

In a further aspect, the present invention relates to a pharmaceutical composition comprising crystalline avapritinib, in particular crystalline avapritinib Form A or Form B or the composition comprising crystalline avapritinib Form A or Form B, or a hydrate of avapritinib, in particular the hydrate Form Hy1 or the composition comprising the hydrate Form Hy1 as defined in any one of the aspects and their corresponding embodiments described above, preferably in an effective and/or predetermined amount, and optionally at least one pharmaceutically acceptable excipient.

Preferably, the predetermined and/or effective amount of crystalline avapritinib, in particular of the crystalline avapritinib Form A or Form B or the composition comprising crystalline avapritinib Form A or Form B, or the hydrate of avapritinib, in particular the hydrate Form Hy1 or the composition comprising the hydrate Form Hy1 as defined in any one of the aspects and their corresponding embodiments described above is in the range of from about 5 to 100 mg, calculated as avapritinib (water free). For example, the predetermined and/or effective amount is selected from the group consisting of 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 90 mg and 100 mg calculated as avapritinib (water free). Preferably, the predetermined and/or effective amount is selected from the group consisting of 5 mg, 10 mg, 30 mg and 100 mg calculated as avapritinib (water free).

In another preferred embodiment, the predetermined and/or effective amount of crystalline avapritinib, in particular of the crystalline avapritinib Form A or Form B or the composition comprising crystalline avapritinib Form A or Form B, or the hydrate of avapritinib, in particular the hydrate Form Hy1 or the composition comprising the hydrate Form Hy1 as defined in any one of the aspects and their corresponding embodiments described above is in the range of from about 100 to 300 mg, calculated as avapritinib (water free). For example, the predetermined and/or effective amount is selected from the group consisting of 100 mg, 125 mg, 150 mg, 175 mg, 200 mg, 225 mg, 250 mg, 275 mg and 300 mg calculated as avapritinib (water free). Preferably, the predetermined and/or effective amount is selected from the group consisting of 100 mg, 200 and 300 mg calculated as avapritinib (water free).

The optional at least one pharmaceutically acceptable excipient, which is comprised in the pharmaceutical composition of the present invention, is preferably selected from the group consisting of fillers, diluents, binders, disintegrants, lubricants, glidants and combinations thereof. Preferably, the at least one pharmaceutically acceptable excipient is selected from the group consisting of microcrystalline cellulose, copovidone, mannitol, croscarmellose sodium, magnesium stearate and combinations thereof. Even more preferably, all of these pharmaceutically acceptable excipients are comprised by the pharmaceutical composition of the present invention.

Preferably, the pharmaceutical composition of the present invention as described above is an oral solid dosage form.

More preferably, the pharmaceutical composition of the present invention as described above is a tablet or a capsule.

In a particular embodiment, the pharmaceutical composition of the present invention as described above is a tablet, preferably a film-coated tablet, even more preferably an immediate-release film-coated tablet.

In another particular embodiment, the pharmaceutical composition of the present invention as described above is a capsule, preferably a hard-gelatin capsule. In a further embodiment, the capsule shell is a gelatin shell or a hydroxypropylmethylcellulose (HPMC) shell, preferably a gelatin shell. In a particular embodiment, the present invention relates to a capsule comprising crystalline avapritinib, such as crystalline avapritinib Form A or Form B or the composition comprising crystalline avapritinib Form A or Form B, or the hydrate of avapritinib, in particular the hydrate Form Hy1 or the composition comprising the hydrate Form Hy1 as defined in any one of the aspects and their corresponding embodiments described above, wherein the capsule does not comprise a pharmaceutically acceptable excipient.

The pharmaceutical compositions of the present invention as defined in any one of the above described embodiments may be produced by standard manufacturing processes, which are well-known to the skilled person including e.g. blending, granulation (wet or dry granulation), tablet compression, film-coating or capsule filling.

The present invention also relates to a packaging comprising the pharmaceutical composition as defined in anyone of the embodiments described above, wherein the packaging is preferably a high density polyethylene bottle.

In a further aspect, the present invention relates to crystalline avapritinib, in particular to crystalline avapritinib Form A or Form B or the composition comprising crystalline avapritinib Form A or Form B, or the hydrate of avapritinib, in particular the hydrate Form Hy1 or the composition comprising the hydrate Form Hy1 or the pharmaceutical composition comprising the same as defined in any one of the aspects and their corresponding embodiments described above for use as a medicament.

In a further aspect, the present invention relates to crystalline avapritinib, in particular to crystalline avapritinib Form A or Form B or the composition comprising crystalline avapritinib Form A or Form B, or the hydrate of avapritinib, in particular the hydrate Form Hy1 or the composition comprising the hydrate Form Hy1 or the pharmaceutical composition comprising the same as defined in any one of the aspects and their corresponding embodiments described above for use in the treatment of gastrointestinal stromal tumors (GIST), including GIST harboring a platelet-derived growth factor receptor alpha (PDGFRA) exon 18 mutation e.g. PDGFRA D842V mutations, advanced systemic mastocytosis (AdvSM), including aggessive systemic mastocytosis (ASM), systemic mastocytosis with and associated hematolocic neoplasm (SM-AHN) and mast cell leukemia (MCL), acute myeloid leukemia (AML), melanoma, seminoma, intercranial germ cell tumors, and mediastinal B-cell lymphoma.

EXAMPLES

The following non-limiting examples are illustrative for the disclosure and are not to be construed as to be in any way limiting for the scope of the invention.

Example 1: Preparation of Crystalline Form A of Avapritinib

Avapritinib (50 mg, e.g. prepared according to the teaching disclosed in WO 2015/057873 A1, in particular the procedure described in Example 7) was heated in a type and amount of solvent according to Table 1. In case no clear solution was obtained, undissolved particles were filtered off. Then the resulting clear solution was allowed to cool to room temperature in order to initiate crystallization. Finally, the obtained crystals were collected by filtration and subsequently dried under vacuum (~35 mbar) for 24 hours.

TABLE 1

| Solvent type and amount used for examples 1A-1Z | | | |
|---|---|---|---|
| Example | Solvent type | Solvent amount [mL] | PXRD |
| A | ethanol | 4 | Form A |
| B | 1-propanol | 2 | Form A |
| C | 2-propanol | 5 | Form A |
| D | n-butanol | 2 | Form A |
| E | 2-butanol | 3 | Form A |
| F | acetone | 3 | Form A |
| G | methyl ethyl ketone | 2 | Form A |
| H | methyl isobutyl ketone | 2 | Form A |
| I | cyclohexanone | 1 | Form A |
| J | dichloromethane | 2 | Form A |
| K | chloroform | 1 | Form A |
| L | methyl acetate | 2 | Form A |
| M | ethyl acetate | 2 | Form A |
| N | isopropyl acetate | 3 | Form A |
| O | n-butyl acetate | 2 | Form A |
| P | isobutyl acetate | 2 | Form A |
| Q | 2-methyl THF | 1 | Form A |
| R | cyclopropyl methyl ether | 3 | Form A |
| S | anisole | 1 | Form A |
| T | toluene | 1.5 | Form A |
| U | xylene (isomers) | 2 | Form A |
| V | mesitylene | 2 | Form A |
| W | chlorobenzene | 2 | Form A |
| X | nitromethane | 1 | Form A |
| Y | dimethyl formamide | 1 | Form A |
| Z | dimethyl sulfoxide | 1 | Form A |

Example 2: Preparation of Crystalline Form B of Avapritinib

Avapritinib (1.28 g, e.g. prepared according to the teaching disclosed in WO 2015/057873 A1, in particular the procedure described in Example 7) was dissolved in isopentanol (40 mL) upon heating to reflux. Then the resulting clear solution was cooled to a temperature of about 0° C. at a rate of −3K/min in order to initiate crystallization. Finally, the obtained crystals were collected by filtration and subsequently dried under vacuum (~35 mbar) for 24 hours.

Example 3: Preparation of Hydrate Form Hy1 of Avapritinib

Method A: Preparation from Methanol/Diisopropylether, Water

Avapritinib (637 mg, e.g. prepared according to the teaching disclosed in WO 2015/057873 A1, in particular the procedure described in Example 7) was dissolved in methanol (50 mL) upon heating to 60° C. The solution was cooled to 0° C. whereat a precipitate occured. Cold diisopropyl ether (40 mL) was added and the suspension was slurried for 20 min at 0° C. Subsequently, the solid was collected by filtration, resuspended in water (5 mL) and slurried at room temperature for 24 hours. After filtration the solid was dried under vacuum (~35 mbar) at room temperature for 17 hours.

Method B: Preparation from Methanol/Water

Avapritinib (164 mg, e.g. prepared according to the teaching disclosed in WO 2015/057873 A1, in particular the procedure described in Example 7) was dissolved in methanol (10 mL) upon heating with a heatgun. The resulting clear solution was filtrated with a syringe filter whereat crystallization occurred immediately. The suspension was cooled in an ice-bath and cold water (10 mL) was added. After 20 min the solid was collected by filtration and dried under vacuum (~35 mbar) at room temperature for 15 hours.

Method C: Preparation in Aqueous Organic Solvent (80% Volume/Volume)

Avapritinib (about 80 mg) was dissolved upon heating in one of the aqueous organic solvents (80% volume/volume) listed in Table 2. The resulting solution was filtered in order to remove residual particles and cooled in an ice-bath. If no precipitate occured after 18 hours an additional amount of water was added. The resulting solid was collected by filtration and dried under vacuum (~35 mbar) at room temperature for 18 hours.

TABLE 2

| Solvent type and amount used for Method C of Example 3 | | |
|---|---|---|
| Aqueous solvent (80% volume/volume) | Amount of aqueous solvent (80% volume/volume) [mL] | Additional amount of anti-solvent (water) [mL] |
| methanol | 4 | 0 |
| ethanol | 4 | 5 |
| isopropanol | 4 | 6 |
| 1,4-dioxane | 1 | 2 |
| THF | 1 | 2 |

Example 4: Powder X-Ray Diffraction

Powder X-ray diffraction was performed with a PANalytical X'Pert PRO diffractometer equipped with a theta/theta coupled goniometer in transmission geometry, Cu-Kalpha$_{1,2}$ radiation (wavelength 0.15419 nm) with a focusing mirror and a solid state PIXcel detector. Diffractograms were recorded at a tube voltage of 45 kV and a tube current of 40 mA, applying a stepsize of 0.013° 2-theta with 40 s per step (255 channels) in the angular range of 2° to 40° 2-Theta at ambient conditions. A typical precision of the 2-Theta values is in the range of ±0.2° 2-Theta, preferably of ±0.1° 2-Theta.

A representative diffractogram of crystalline avapritinib Form A according to the present invention is displayed in FIG. 1 and the corresponding reflection list (peak list) from 2 to 30° 2-Theta is provided in Table 3 below.

TABLE 3

| Reflection (peak) positions of crystalline avapritinib Form A according to the present invention in the range of from 2 to 30° 2-Theta; A typical precision of the 2-Theta values is in the range of ±0.2° 2-Theta, preferably of +0.1° 2-Theta. Reflection position [° 2-Theta] |
|---|
| 3.8 |
| 10.1 |
| 11.5 |
| 13.8 |
| 15.3 |
| 16.2 |
| 16.7 |
| 17.3 |
| 18.0 |
| 18.1 |
| 18.5 |
| 19.7 |
| 20.0 |
| 20.3 |
| 21.5 |
| 22.9 |
| 23.1 |

TABLE 3-continued

| Reflection (peak) positions of crystalline avapritinib Form A according to the present invention in the range of from 2 to 30° 2-Theta; A typical precision of the 2-Theta values is in the range of ±0.2° 2-Theta, preferably of +0.1° 2-Theta. Reflection position [° 2-Theta] |
|---|
| 23.8 |
| 24.3 |
| 25.2 |
| 25.8 |
| 26.2 |
| 27.8 |
| 28.2 |
| 28.5 |
| 29.6 |

A representative diffractogram of crystalline avapritinib Form B according to the present invention is displayed in FIG. 6 and the corresponding reflection list (peak list) from 2 to 30° 2-Theta is provided in Table 4 below.

TABLE 4

| Reflection (peak) positions of crystalline avapritinib Form B according to the present invention in the range of from 2 to 30° 2-Theta; A typical precision of the 2-Theta values is in the range of ±0.2° 2-Theta, preferably of +0.1° 2-Theta. Reflection position [° 2-Theta] |
|---|
| 3.6 |
| 7.1 |
| 10.1 |
| 10.7 |
| 11.3 |
| 12.2 |
| 13.4 |
| 14.3 |
| 14.6 |
| 16.0 |
| 16.7 |
| 16.9 |
| 17.3 |
| 17.8 |
| 18.2 |
| 18.9 |
| 19.2 |
| 19.6 |
| 20.0 |
| 20.3 |
| 20.8 |
| 21.2 |
| 21.7 |
| 21.9 |
| 22.0 |
| 22.3 |
| 22.7 |
| 23.3 |
| 23.7 |
| 24.0 |
| 24.3 |
| 24.6 |
| 24.9 |
| 25.6 |
| 26.6 |
| 27.2 |
| 27.8 |
| 28.2 |
| 28.7 |
| 29.0 |
| 29.5 |

A representative diffractogram of avapritinib hydrate Form Hy1 according to the present invention is displayed in FIG. 11 and the corresponding reflection list (peak list) from 2 to 30° 2-Theta is provided in Table 5 below.

TABLE 5

| Reflection (peak) positions of avapritinib hydrate Form Hy1 according to the present invention in the range of from 2 to 30° 2-Theta; A typical precision of the 2-Theta values is in the range of ±0.2° 2-Theta, preferably of +0.1° 2-Theta. Reflection position [° 2-Theta] |
|---|
| 5.3 |
| 9.3 |
| 10.4 |
| 12.0 |
| 13.9 |
| 14.7 |
| 15.2 |
| 16.1 |
| 17.4 |
| 17.9 |
| 18.1 |
| 18.7 |
| 18.9 |
| 20.9 |
| 21.4 |
| 21.8 |
| 22.3 |
| 22.8 |
| 23.4 |
| 24.0 |
| 24.7 |
| 25.2 |
| 25.7 |
| 26.0 |
| 27.3 |
| 29.7 |

Figure 10:
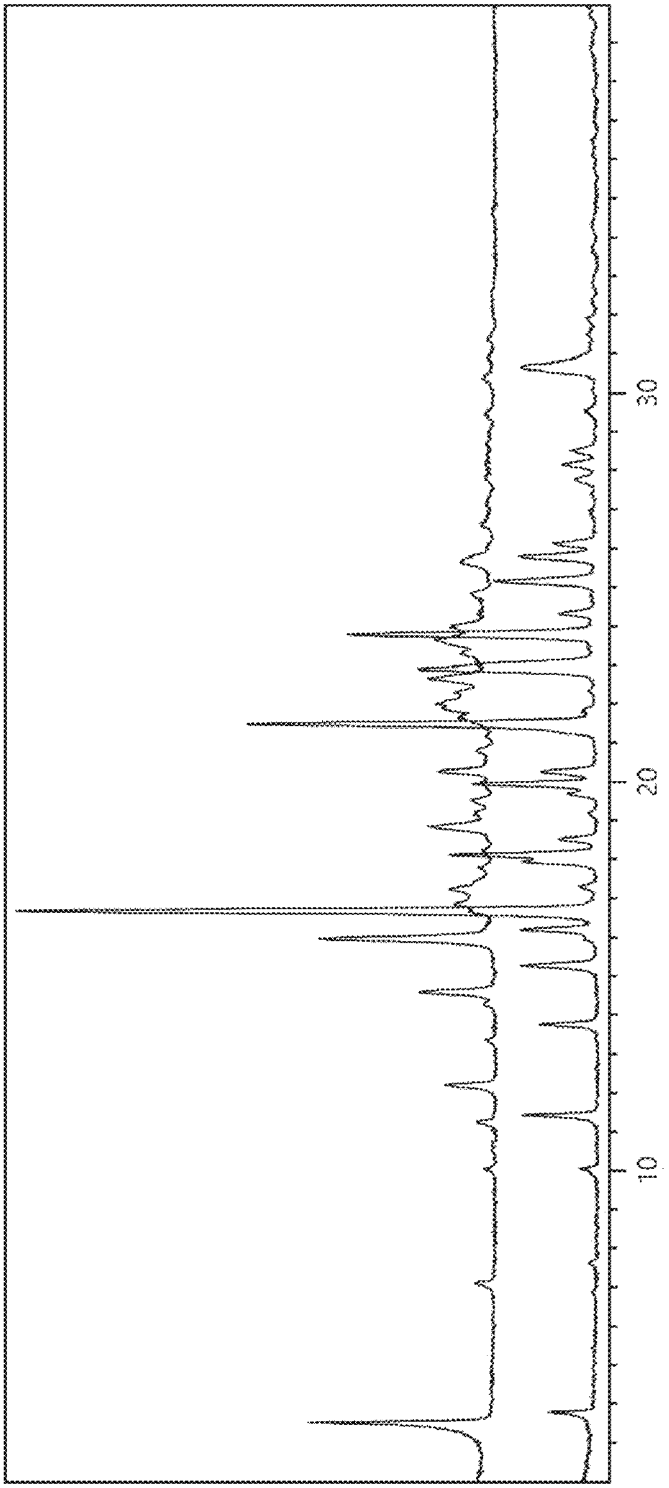
FIG. 10: illustrates a comparison of representative PXRDs of crystalline avapritinib Form A (bottom) and crystalline avapritinib Form B (top) according to the present invention. The x-axis shows the scattering angle in °2-Theta. The powder X-ray diffractogram of Form B was shifted along the y-axis to separate the diffractograms for clarity. The y-axis is therefore arbitrary and was not labeled.

FIG. 10 illustrates an overlay of the PXRDs of Form A and Form B of the present invention. As can be seen both forms can be readily distinguished from each other by powder X-ray diffractometry. For example, the PXRD of avapritinib Form A possesses a refelection at (15.3±0.2)°2-Theta, whereas no reflection is visible in the PXRD of avapritinib Form B in this range. On the other hand, the PXRD of avapritinib Form B displays i.a. reflections at 2-Theta angles of (7.1±0.2)°, (10.7±0.2)°, (12.2±0.2)°, (14.3±0.2)°, (14.6±0.2)°, (19.2±0.2)°, (20.8±0.2)°, (22.0±0.2)°, (22.3±0.2)°, (27.2±0.2)° and (29.0±0.2)°, e.g. at ranges, where avapritinib Form A shows no reflections.

Figure 16:
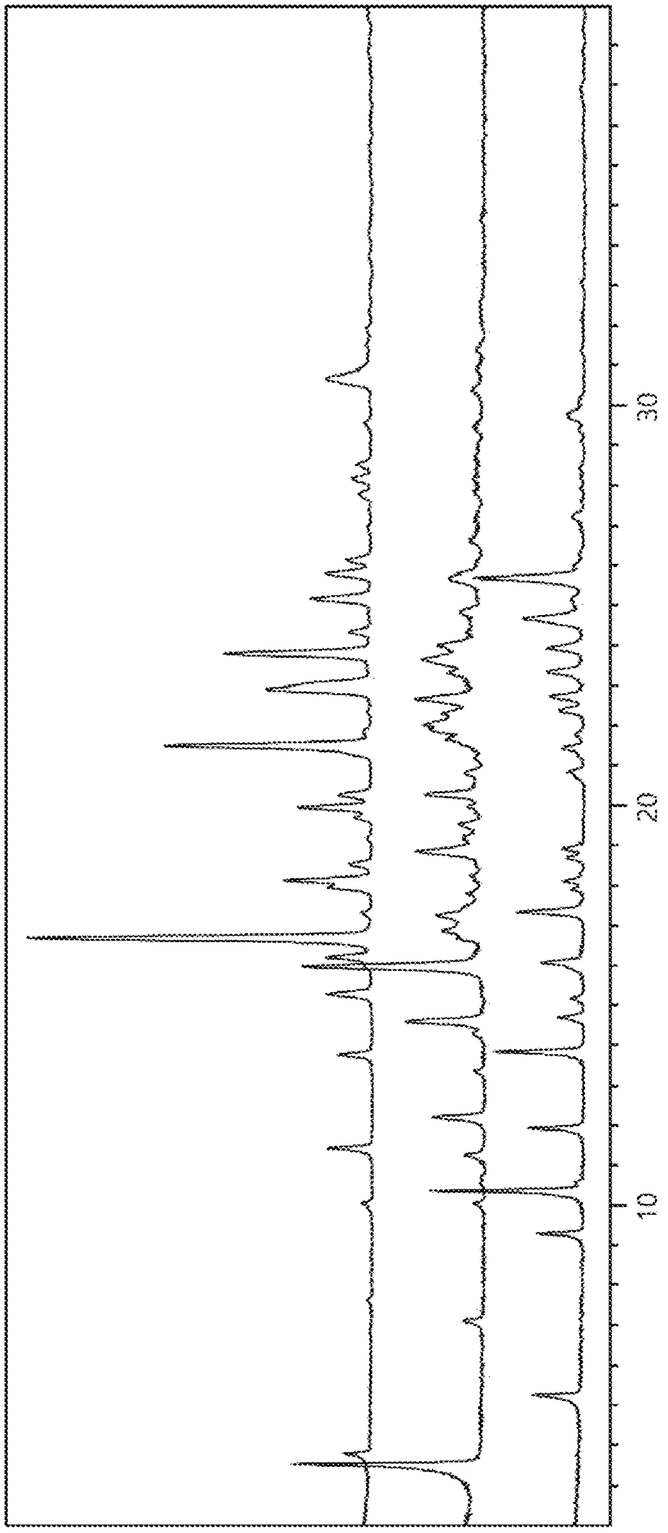
FIG. 16: illustrates a comparison of representative PXRDs of crystalline avapritinib Form A (top), crystalline avapritinib Form B (middle) and the avapritinib hydrate Form Hy1 (bottom) according to the present invention. The x-axis shows the scattering angle in °2-Theta. The powder X-ray diffractograms of Form A and Form B were shifted along the y-axis to separate the diffractograms for clarity. The y-axis is therefore arbitrary and was not labeled.

FIG. 16 displays an overlay of the PXRDs of Form A, Form B and hydrate Form Hy1. As can be seen Form Hy1 can be readily distinguished from Form A and Form B. For example, Form Hy1 shows reflections at 2-Theta angles of (5.3±0.2)° and (9.3±0.2)° whereas Form A and Form B of avapritinib show no reflections in these ranges. On the other hand Form Hy1 possesses no reflection at 2-Theta angles below (5.3±0.2)°, whereas Form A and Form B of avapritinib exhibit a reflection at 2-Theta angles of (3.8±0.2)° and (3.6±0.2)°, respectively.

Example 5: Differential Scanning Calorimetry (DSC)

DSC was performed on a Mettler Polymer DSC R instrument. The samples (3.89 mg Form A, 4.60 mg Form B, 2.24 mg Form Hy1) were each heated in a 40 microliter aluminium pan with a pierced aluminium lid from 25 to 250° C. at a rate of 10 K/min. Nitrogen (purge rate 50 mL/min) was used as purge gas.

Figure 2:
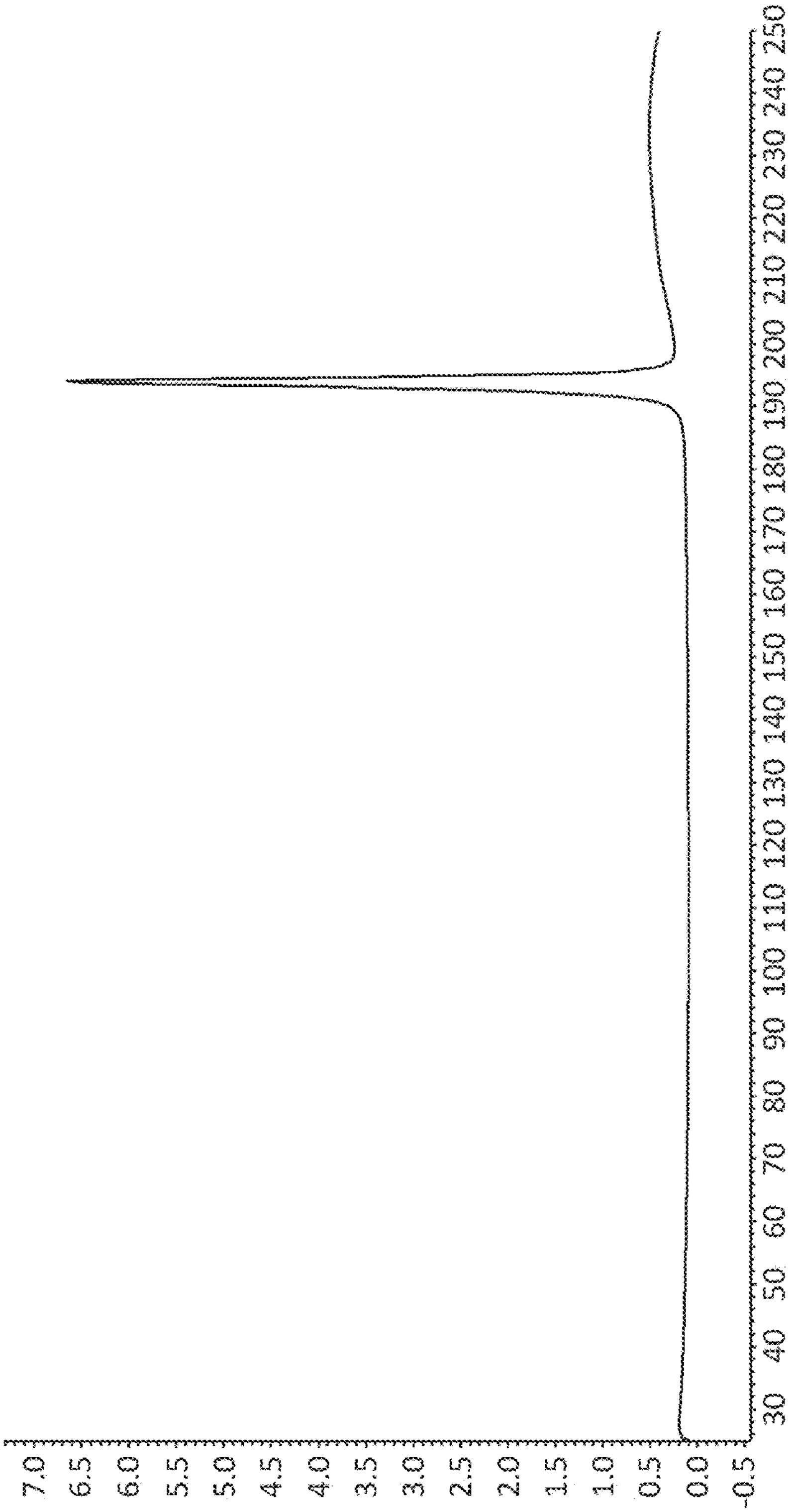
FIG. 2: illustrates a representative DSC curve of crystalline avapritinib Form A according to the present invention. The x-axis shows the temperature in degree Celsius (° C.), the y-axis shows the heat flow rate in Watt per gram (W/g) with endothermic peaks going up.

The DSC curve of Form A (see FIG. 2) shows a single endothermic peak with a peak onset at temperature of about 192° C. and a peak maximum at a temperature of about 193° C., which is due to the melting of the sample. The anhydrous and non-solvated nature of the avapritinib Form A and its excellent thermal stability are evidenced by the fact that no thermal events indicating phase changes, desolvation or decomposition are detectable until the sample melts.

Figure 7:
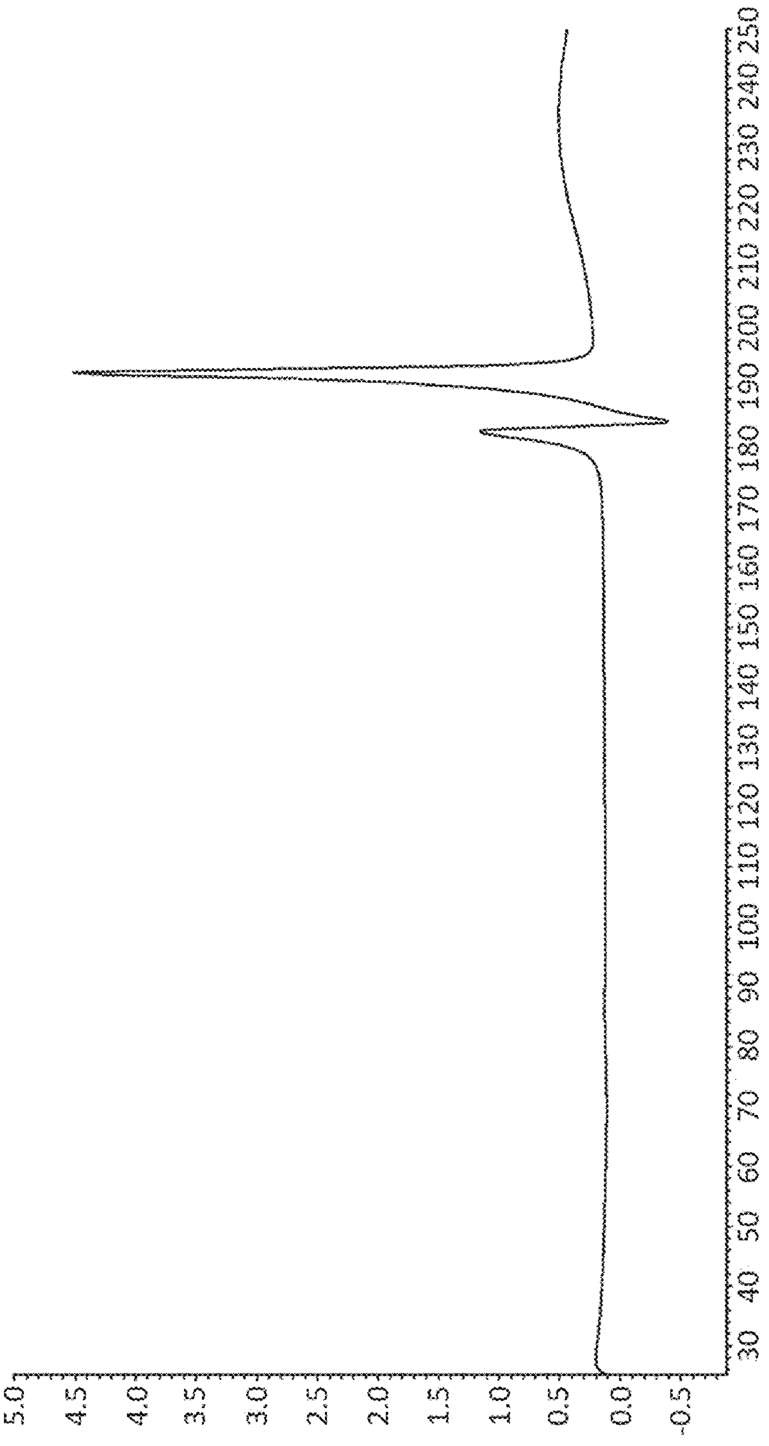
FIG. 7: illustrates a representative DSC curve of crystalline avapritinib Form B according to the present invention. The x-axis shows the temperature in degree Celsius (° C.), the y-axis shows the heat flow rate in Watt per gram (W/g) with endothermic peaks going up.

The DSC curve of Form B (see FIG. 7) shows multiple thermal events starting with an endothermic peak having a peak onset at temperature of about 180° C. and a peak maximum at a temperature of about 182° C., immediately followed by an exothermic peak having a peak minimum at a temperature of about 184° C. and a second endothermic peak having a peak maximum at a temperature of about 191° C. According to DSC analysis also Form B shows excellent thermal stability as no thermal events were detectable up to a temperature as high as about 180° C.

Figure 13:
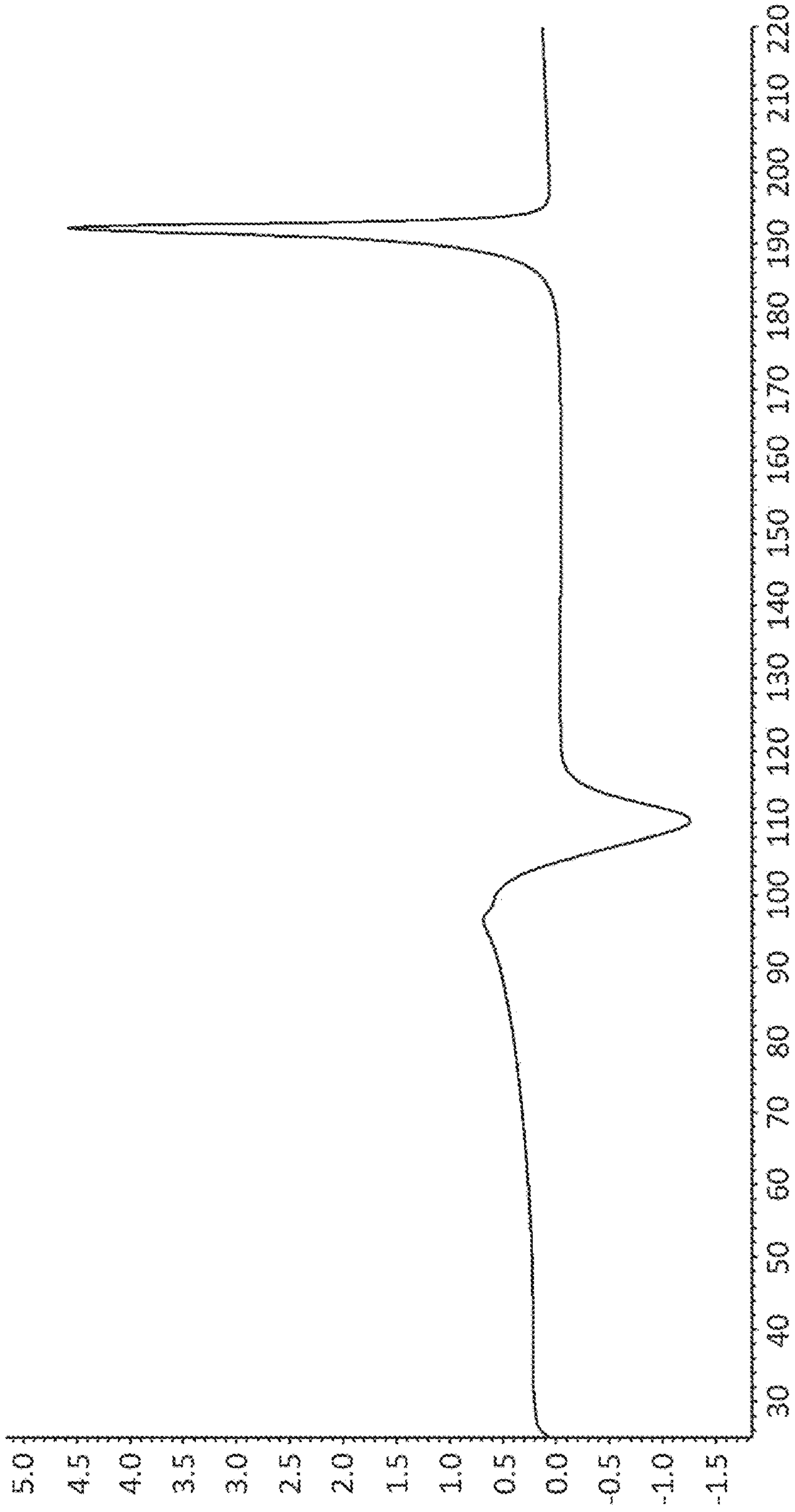
FIG. 13: illustrates a representative DSC curve of the avapritinib hydrate Form Hy1 according to the present invention. The x-axis shows the temperature in degree Celsius (° C.), the y-axis shows the heat flow rate in Watt per gram (W/g) with endothermic peaks going up.

The DSC of hydrate Form Hy1 (see FIG. 13) shows multiple thermal events starting with a broad endothermic peak having a peak onset at a temperature of about 78° C. and a peak maximum at a temperature of about 97° C., which indicates a dehydration event. Immediately after this first broad endotherm an exothermic peak having a peak minimum at a temperature of about 110° C. follows, which indicates a rearrangement of the molecules to avapritinib Form A. Finally, Form A melts as indicated by a second endothermic peak with a peak onset at temperature of about 190° C. and a peak maximum at a temperature of about 192° C.

Example 6: Thermogravimetric Analysis (TGA)

TGA was performed on a Mettler TGA/DSC 1 instrument. The samples (8.29 mg Form A, 8.11 mg Form B, 4.12 mg Form Hy1) were each weighed into a 100 microliter aluminum pan closed with an aluminum lid. The lid was automatically pierced at the beginning of the measurement. The samples were each heated from 25 to 250° C. at a rate of 10 K/min. Nitrogen (purge rate 50 mL/min) was used as purge gas.

Figure 3:
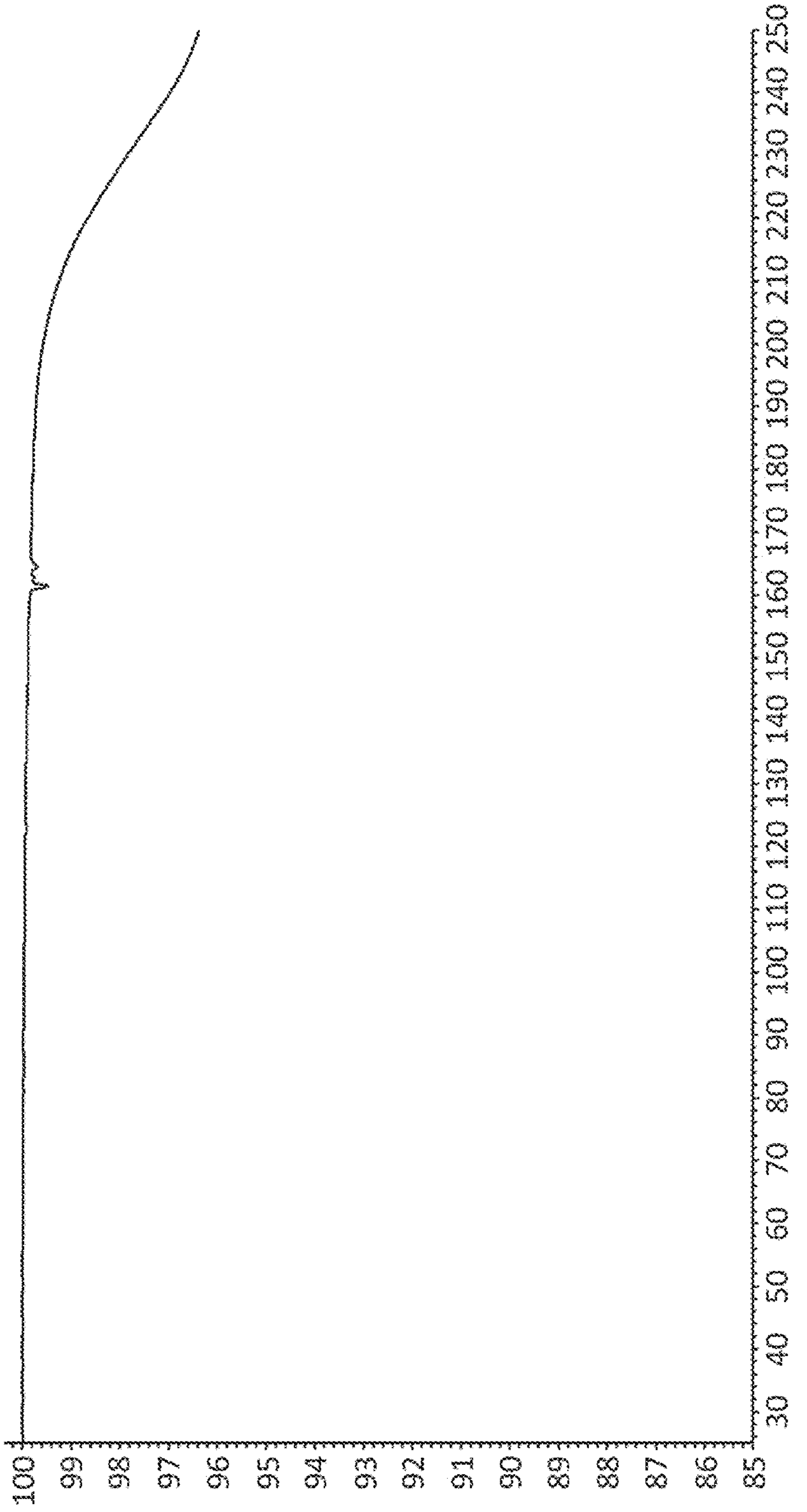
FIG. 3: illustrates a representative TGA curve of crystalline avapritinib Form A of the present invention. The x-axis shows the temperature in degree Celsius (° C.), the y-axis shows the mass (loss) of the sample in weight percent (w-%).
Figure 4:
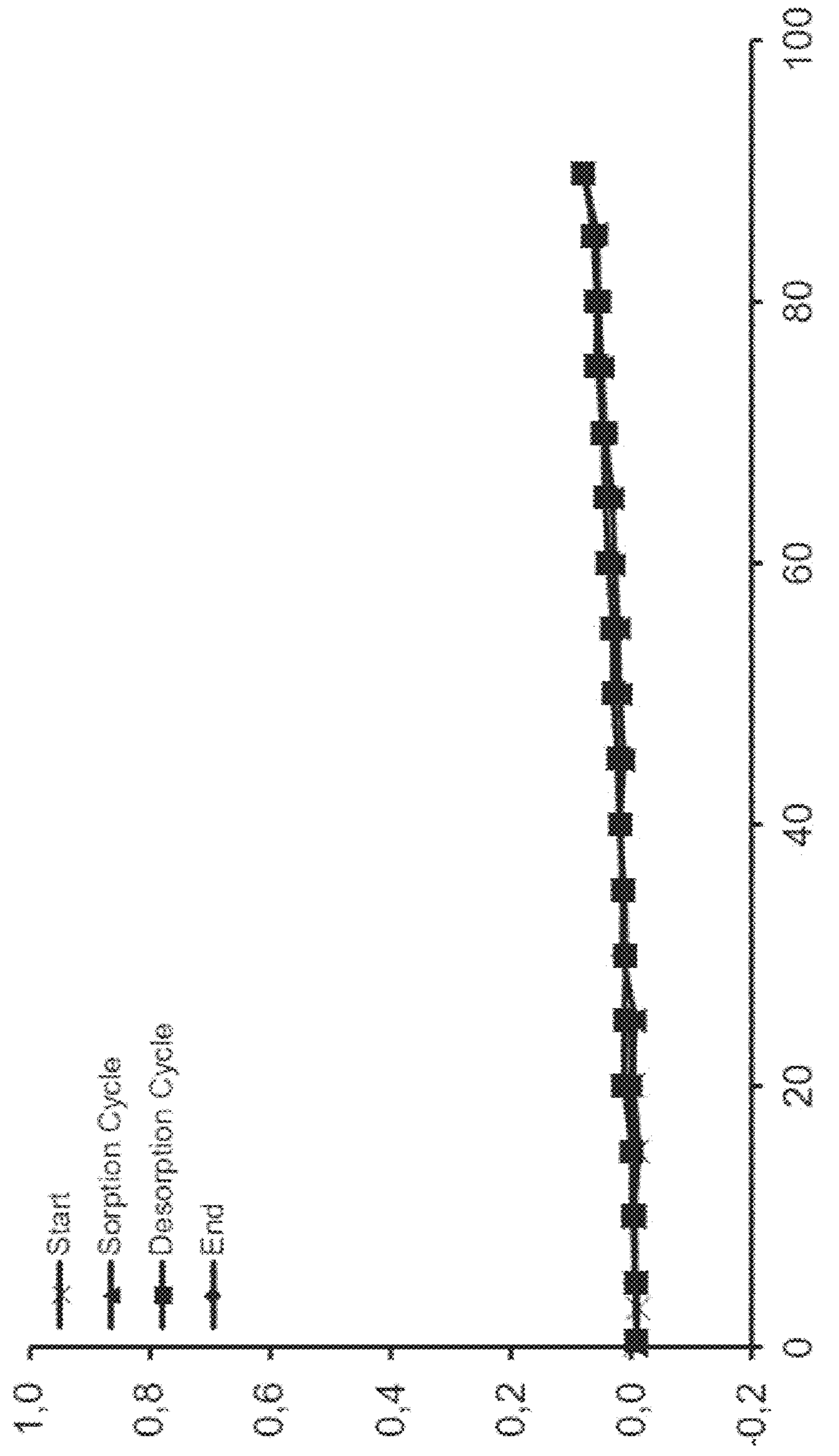
FIG. 4: illustrates representative GMS isotherms of crystalline avapritinib Form A of the present invention in the range of from 0 to 90% relative humidity. The x-axis displays the relative humidity in percent (%) measured at a temperature of (25.0±0.1)° C., the y-axis displays the equilibrium mass change in weight percent (w-%).

The TGA curve of Form A (see FIG. 3) shows no significant mass loss until the sample melts. For example a mass loss of only about 0.3 weight % up to a temperature of about 190° C. was observed for Form A which further proves the presence of an anhydrous and non-solvated crystal form.

Figure 8:
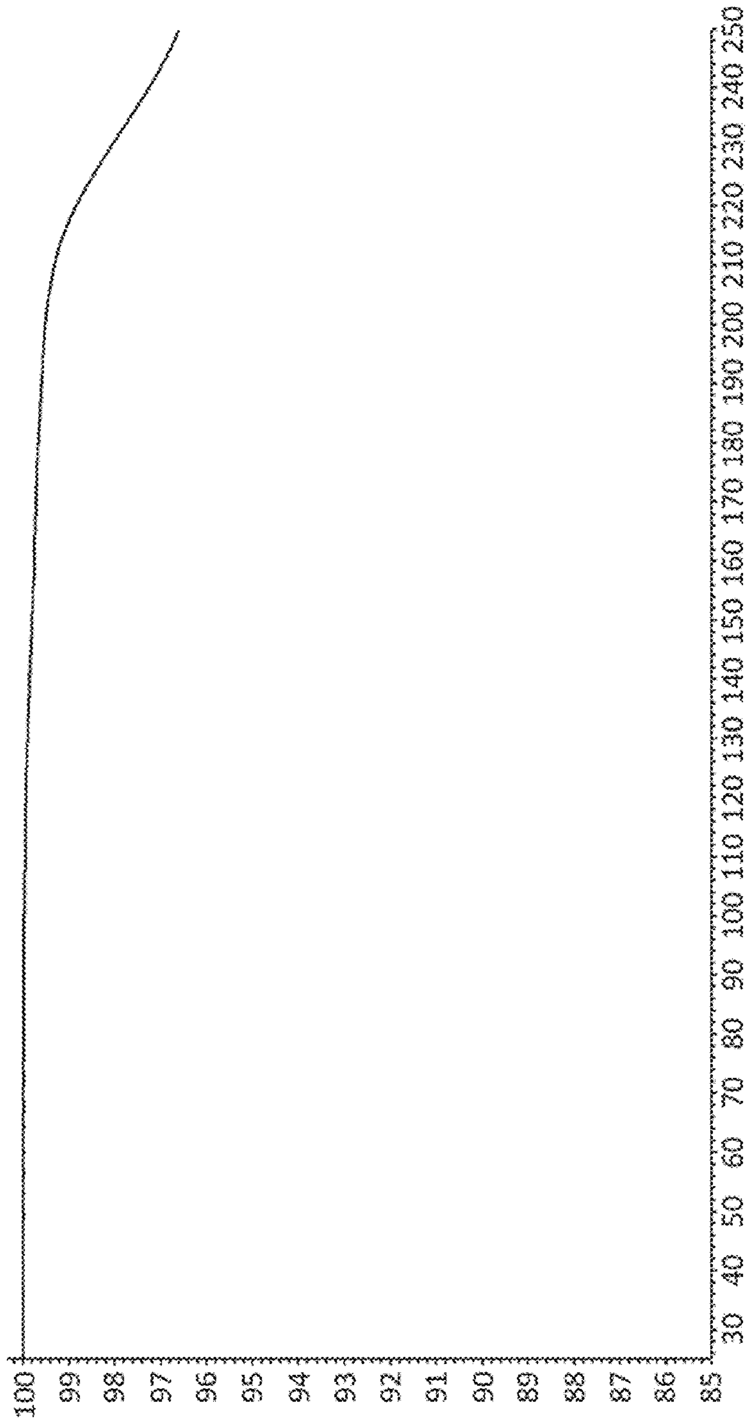
FIG. 8: illustrates a representative TGA curve of crystalline avapritinib Form B of the present invention. The x-axis shows the temperature in degree Celsius (° C.), the y-axis shows the mass (loss) of the sample in weight percent (w-%).

The TGA curve of Form B (see FIG. 8) shows no significant mass loss until the first endothermic signal. For example a mass loss of only about 0.3 weight-% up to a temperature of about 180° C. was observed for Form B which further proves the presence of an anhydrous and non-solvated crystal form.

Figure 14:
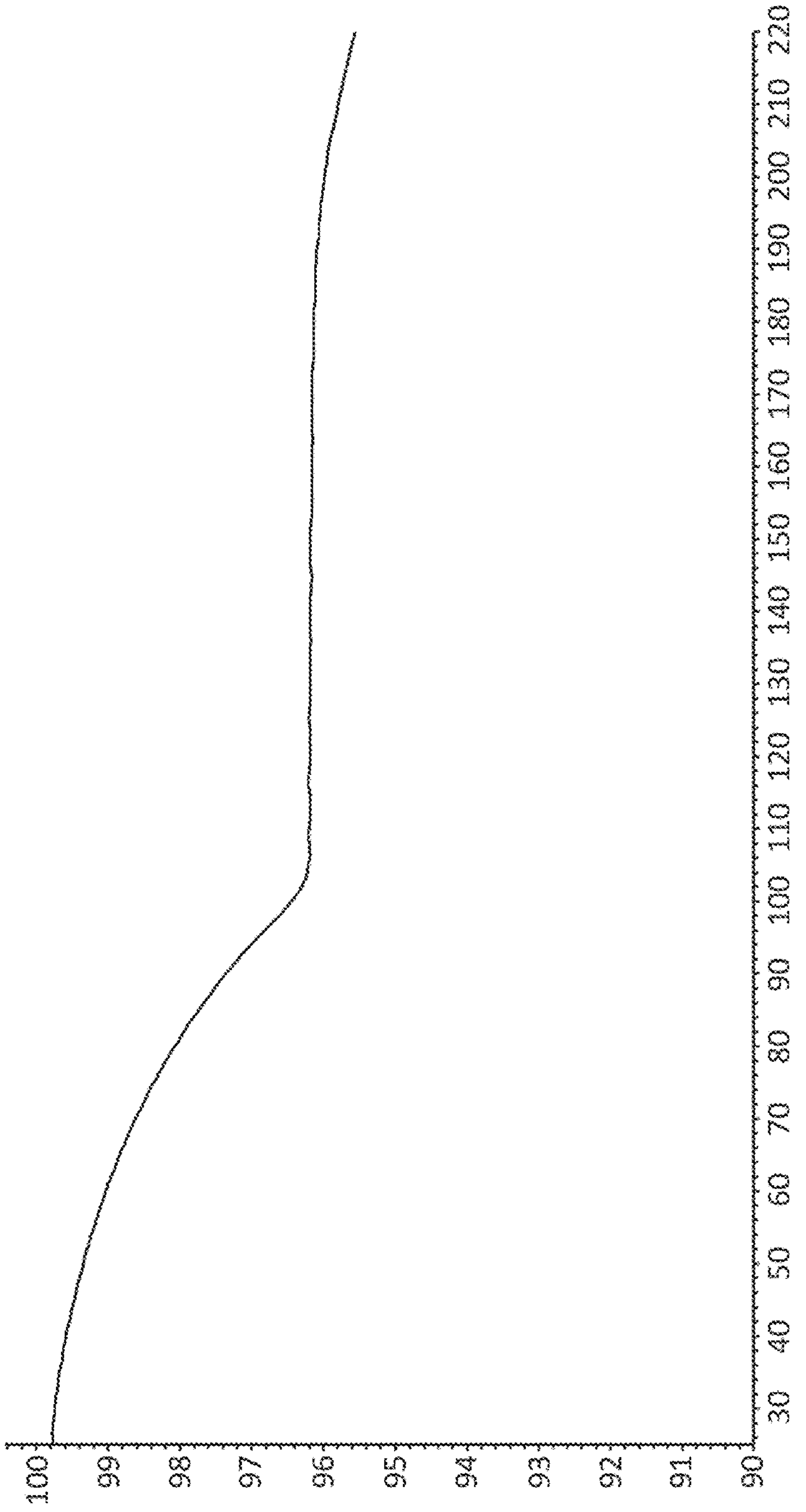
FIG. 14: illustrates a representative TGA curve of the avapritinib hydrate Form Hy1 of the present invention. The x-axis shows the temperature in degree Celsius (° C.), the y-axis shows the mass (loss) of the sample in weight percent (w-%).

The TGA curve of Form Hy1 (see FIG. 14) shows a mass loss of 3.5 weight-% from the beginning of the measurement until a temperature of about 110° C., which corresponds to approximately 1 mol equivalent of water.

Example 7: Gravimetric Moisture Sorption

Moisture sorption isotherms were recorded along with other samples with an SPSx-1μ moisture sorption analyzer (ProUmid, Ulm). The measurement cycle was started at ambient relative humidity (RH) of 25% (Form A) or 40% (Form B and Form Hy1). Relative humidity was then decreased to 5% in 5% steps, followed by a further decrease to 3% and to 0%. Afterwards RH was increased from 0% to 90% in a sorption cycle and decreased to 0% in a desorption cycle in 5% steps. Finally, the RH was increased to a relative humidity of 25% (Form A) or 40% (Form B and Form Hy1) in 5% steps. The time per step was set to a minimum of 2 hours and a maximum of 6 hours. If an equilibrium condition with a constant mass of +0.01% within 1 hour was reached before the maximum time for all examined samples the sequential humidity step was applied before the maximum time of 6 hours. If no equilibrium was achieved the consecutive humidity step was applied after the maximum time of 6 hours. The temperature was (25±0.1)° C.

Figure 5:
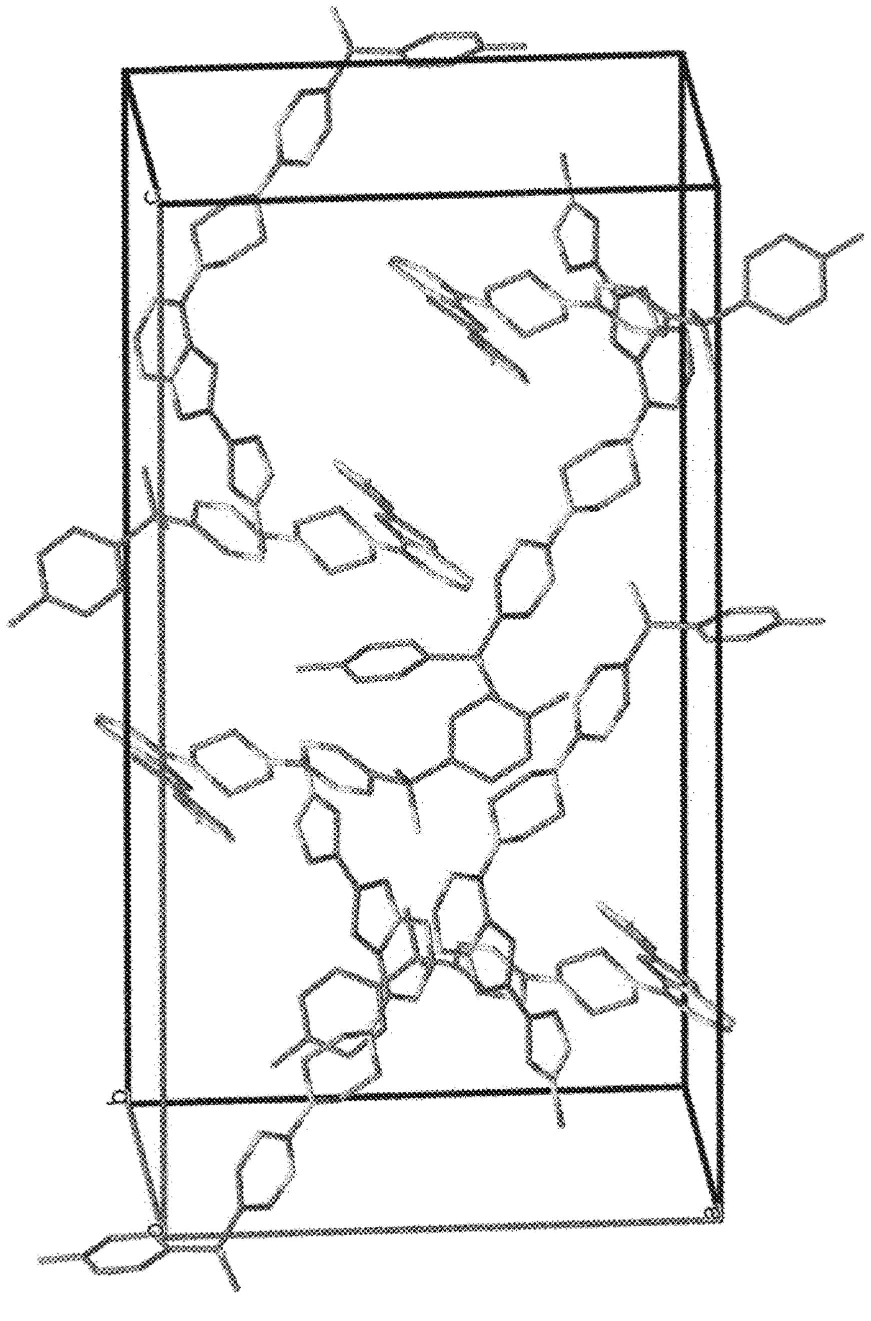
FIG. 5: illustrates the unit cell of crystalline avapritinib Form A of the present invention. Hydrogen atoms are omitted for clarity.

The corresponding moisture sorption and desorption isotherms of avapritinib Form A of the present invention are displayed in FIG. 5. As can be seen, Form A shows almost no interaction with water vapor. A mass change of only about 0.1 weight % during the sorption cycle in the range of 0-90% RH indicates that Form A is non-hygroscopic. The absence of a significant hysteresis between sorption and desorption curves further indicates that Form A preserves its crystal structure throughout the whole experiment. Powder X-ray diffraction performed after the GMS experiment confirmed the presence of avapritinib Form A.

Figure 9:
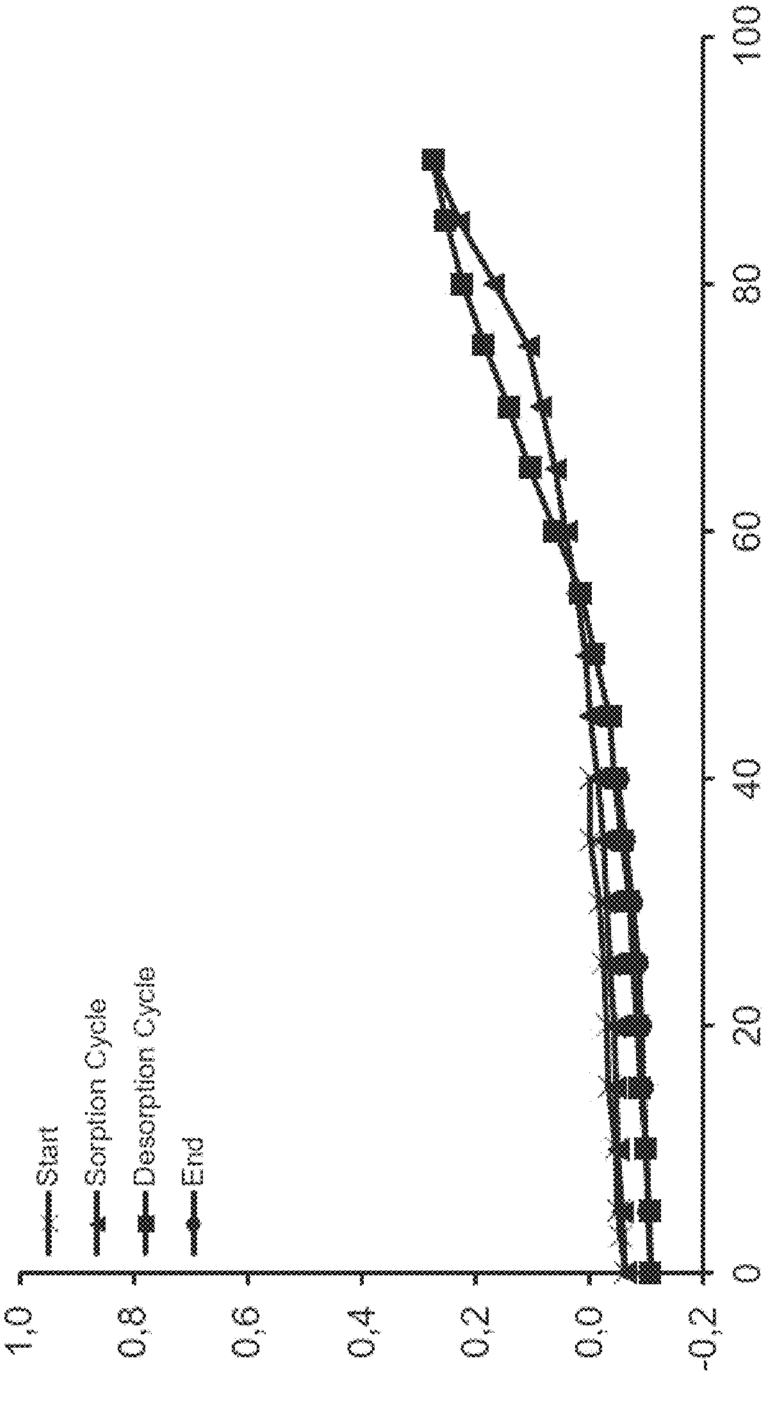
FIG. 9: illustrates representative GMS isotherms of crystalline avapritinib Form B of the present invention in the range of from 0 to 90% relative humidity. The x-axis displays the relative humidity in percent (%) measured at a temperature of (25.0±0.1)° C., the y-axis displays the equilibrium mass change in weight percent (w-%).

The respective moisture sorption and desorption isotherms of avapritinib Form B of the present invention are displayed in FIG. 9. As can be seen Form B shows almost no interaction with water vapor. A mass change of only about 0.3 weight % during the sorption cycle in the range of 0-90% RH indicates that Form B is only slightly hygroscopic. The absence of a significant hysteresis between sorption and desorption curves further indicates that Form B preserves its crystal structure throughout the whole experiment. Powder X-ray diffraction performed after the GMS experiment confirmed the presence of avapritinib Form B.

Figure 15:
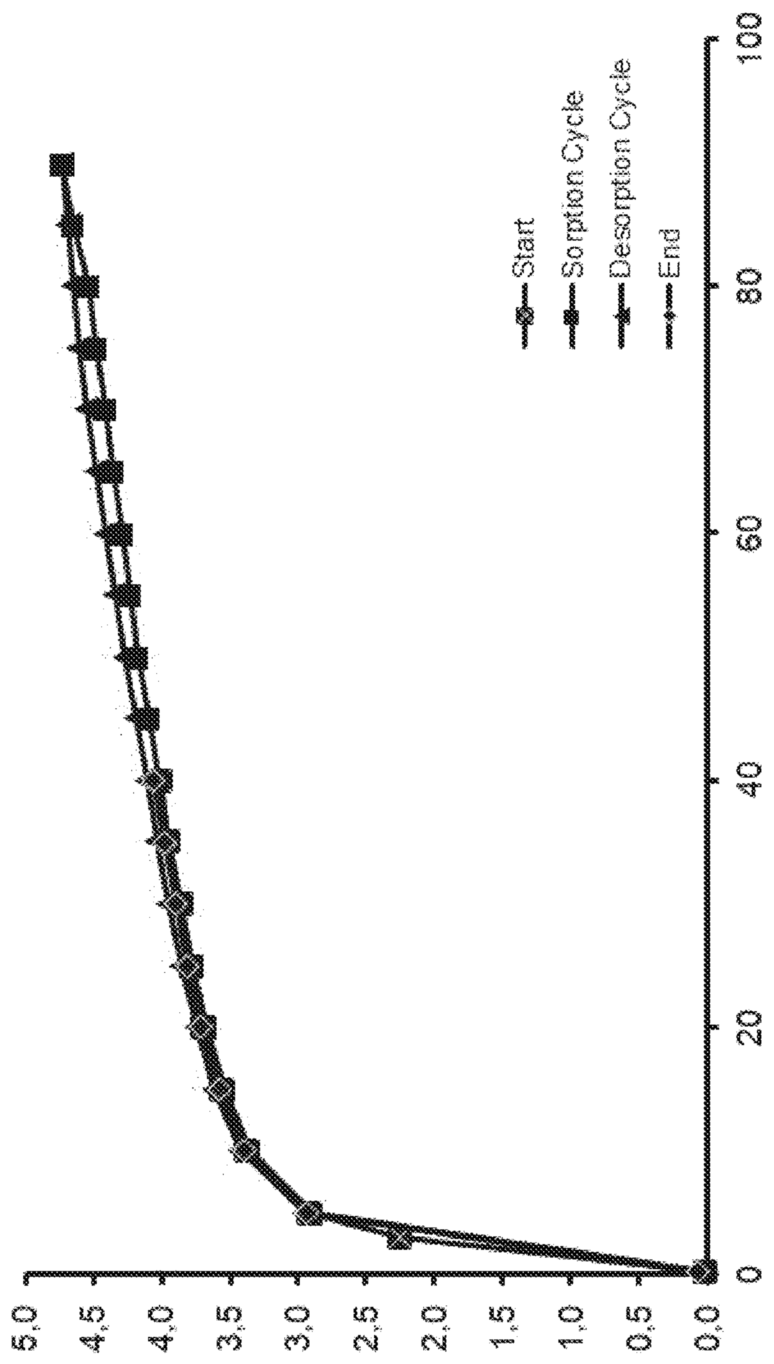
FIG. 15: illustrates representative GMS isotherms of the avapritinib hydrate Form Hy1 of the present invention in the range of from 0 to 90% relative humidity. The x-axis displays the relative humidity in percent (%) measured at a temperature of (25.0±0.1)° C., the y-axis displays the equilibrium mass change in weight percent (w-%).

The respective moisture sorption and desorption isotherms of avapritinib hydrate Form Hy1 of the present invention are displayed in FIG. 15. As can be seen Form Hy1 shows only slight interaction with water vapor. A mass change of about 1.4 weight % during the sorption cycle in the range of 10-90% RH indicates that Form Hy1 is only slightly hygroscopic. Only at very dry conditions below 10% RH water is reversibly released from the crystal structure. Powder X-ray diffraction performed after the GMS experiment confirmed the presence of avapritinib Form Hy1.

Example 8: Single Crystal X-Ray Diffraction

Intensity data for the crystal structure of avapritinib Form A were collected at 193 K, using Mo radiation (λ=0.71073), on an Oxford Diffraction Gemini-R Ultra diffractometer operated by the CrysAlisPro software (Rigaku OD, 2015). The data were corrected for absorption effects by means of comparison of equivalent reflections. The structure was solved with the direct methods procedure implemented in SHELXT and refined by full-matrix least squares refinement on F2 using SHELXL-2014. [Sheldrick, Acta Cryst. A71 (2015), 3-8 and C71 (2015), 3-8].

Example 9: FTIR Spectroscopy

FTIR spectroscopy was performed on a MKII Golden Gate™ Single Reflection Diamond ATR cell with a Bruker Tensor 27 FTIR spectrometer with 4 $cm^{-1}$ resolution at RT. To record a spectrum a spatula tip of the sample was applied to the surface of the diamond in powder form. Then the sample was pressed onto the diamond with a sapphire anvil and the spectrum was recorded. A spectrum of the clean diamond was used as background spectrum.

A representative FTIR spectrum of avapritinib hydrate Form Hy1 according to the present invention is displayed in FIG. 12 and the corresponding peak list is provided in Table 6 below.

TABLE 6

| FTIR peak list of avapritinib hydrate Form Hy1 according to the present invention; a typical precision of the wavenumbers is in the range of ±4 $cm^{-1}$, preferably of ±2 $cm^{-1}$. Wavenumber [$cm^4$] |
|---|
| 3373 |
| 2981 |
| 2863 |
| 1584 |
| 1537 |
| 1491 |
| 1441 |
| 1426 |
| 1349 |
| 1307 |
| 1248 |
| 1220 |
| 1186 |
| 1165 |
| 1123 |
| 1085 |
| 1010 |
| 991 |
| 959 |
| 926 |
| 896 |
| 837 |
| 796 |
| 762 |
| 722 |
| 656 |
| 634 |
| 616 |

Example 10: Thermodynamic Relationship of Avapritinib Form A and Form B of the Present Invention

Slurry Experiments

Form A and Form B of avapritinib were each slurried in aqueous isopropanol [4 mL, 3:1 (volume:volume)] at 0° C., 20° C. and 40° C., respectively. Samples were taken after 1 and 5 days and investigated by powder-X-ray diffraction. The results are summarized in Table 7.

TABLE 7

Results of slurry experiments

| | 0° C. | | | 20° C. | | | 40° C. | | |
|---|---|---|---|---|---|---|---|---|---|
| Initial Form | Weight [mg] | 1 day | 5 days | Weight [mg] | 1 day | 5 days | Weight [mg] | 1 day | 5 days |
| A | 69 | A | A | 71 | A | A | 77 | A | A |
| B | 73 | B + A | A + B | 70 | A | A | 79 | A | A |

As can be seen from Table 7 Form A remained stable under all applied conditions, whereas Form B partially converted to Form A at 0° C. and fully converted to Form A at 20° C. and 40° C. already after 1 day.

DSC Experiment at Heating Rate 1 K/Min

The DSC experiment of Example 5 was repeated with Form B this time using a lower heating rate of 1 K/min instead of 10 K/min.

DSC was performed on a Mettler Polymer DSC R instrument. The sample (3.54 mg Form B) was heated in a 40 microliter aluminium pan with a pierced aluminium lid from 25 to 250° C. at a rate of 1 K/min. Nitrogen (purge rate 50 mL/min) was used as purge gas.

Figure 17:
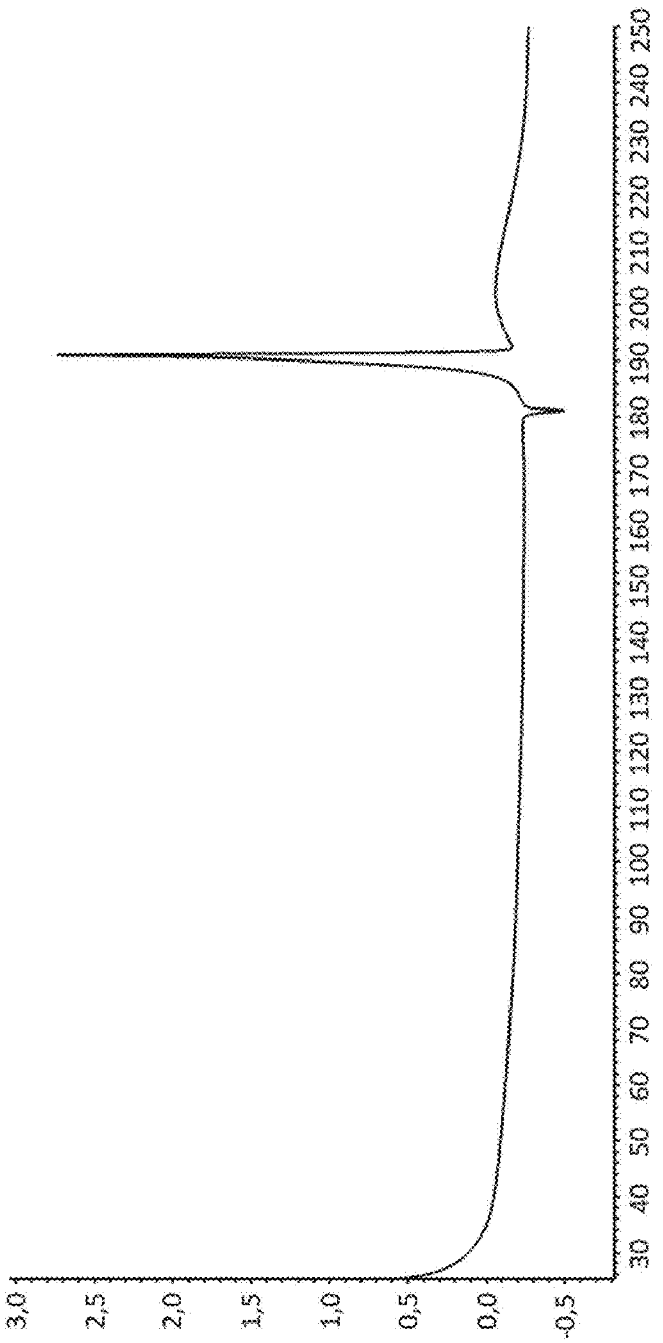
FIG. 17: illustrates a DSC curve of crystalline avapritinib Form B according to the present invention measured at a heating rate of 1 K/min. The x-axis shows the temperature in degree Celsius (° C.), the y-axis shows the heat flow rate in Watt per gram (W/g) with endothermic peaks going up.

At a heating rate of 1 K/min, the DSC curve of Form B (see FIG. 17) shows an exothermic peak having a peak onset at a temperature of about 180° C. and a peak minimum at a temperature of about 181° C., which is due to a solid-solid transformation of Form B to Form A. Thereafter, Form A melts which is indicated by an endothermic peak having an onset temperature of about 190° C. and peak maximum at a temperature of about 191° C.

The results of the performed experiments reveal that avapritinib Form A and B are monotropically related with Form A being the stable form below its melting point.

Example 11: Storage Stability Under Various Stress Conditions

Avapritinib Form A, Form B and hydrate Form Hy1 were each subjected to the various stress conditions listed in Table 8 for 6 months and the samples were investigated by powder X-ray diffraction.

TABLE 8

Results of stress tests after 6 months

| initial | 25° C./ 60% RH | 30° C./ 65% RH | 40° C./ 75% RH | RT/ 97% RH |
|---|---|---|---|---|
| A | A | A | A | A |
| B | B | B | B | B |
| Hy1 | Hy1 | Hy1 | Hy1 | Hy1 |

As can be seen from Table 8 all forms remained stable under all conditions and preserved their crystal structures.

The invention claimed is:

1. Avapritinib according to the chemical structure as depicted in Formula (I)

Formula (I)

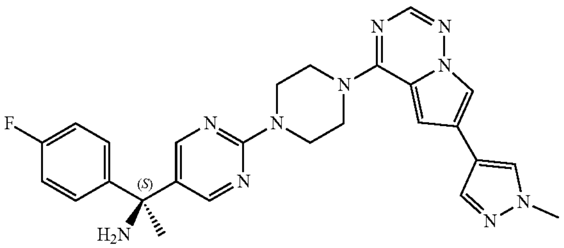

, characterized in that said avapritinib is crystalline, wherein said crystalline avapritinib is in crystalline Form B, and said crystalline Form B is characterized by having a powder X-ray diffractogram comprising reflections at 2-Theta angles of (3.6±0.2)°, (16.0±0.2)° and (14.6±0.2)°, when measured at a temperature in the range of from 20 to 30° C. with Cu-Kalpha$_{1,2}$ radiation having a wavelength of 0.15419 nm.

2. Crystalline avapritinib according to claim 1, characterized in that said avapritinib is anhydrous.

3. Crystalline avapritinib according to claim 1 characterized in that said avapritinib is non-solvated.

4. Crystalline avapritinib according to claim 1, having a differential scanning calorimetry curve comprising an endothermic peak having a peak onset at a temperature of (180±1)° C., when measured at a heating rate of 10 K/min.

5. A composition comprising crystalline avapritinib according to claim 1, characterized by comprising at most 20 weight-% of any other solid-state form of avapritinib, based on the weight of the composition.

6. The composition of claim 5, characterized by having a PXRD comprising no reflections at 2-Theta angles of (15.3±0.2)°, when measured at a temperature in the range of from 20 to 30° C. with Cu-Kalpha$_{1,2}$ radiation having a wavelength of 0.15419 nm.

7. A pharmaceutical composition comprising crystalline avapritinib as defined in claim 1 and at least one pharmaceutically acceptable excipient.

8. The pharmaceutical composition of claim 7, wherein the at least one pharmaceutically acceptable excipient is selected from the group consisting of microcrystalline cellulose, copovidone, mannitol, croscarmellose sodium, magnesium stearate and combinations thereof.

9. The pharmaceutical composition of claim 7, wherein the at least one pharmaceutically acceptable excipient comprises a mixture of microcrystalline cellulose, copovidone, mannitol, croscarmellose sodium, and magnesium stearate.

10. An oral solid dosage form comprising the crystalline avapritinib of claim 1.

11. A tablet form comprising the crystalline avapritinib of claim 1.

12. A film-coated tablet form comprising the crystalline avapritinib of claim 1.

13. An immediate-release, film-coated tablet form comprising the crystalline avapritinib of claim 1.

14. A process for the preparation of a pharmaceutical composition comprising blending avapritinib as defined in claim 1 with at least one pharmaceutically acceptable excipient.

15. A method of therapeutic treatment against systemic mastocytosis, GIST (gastrointestinal stromal tumors), AML (acute myeloid leukemia), melanoma, seminoma, intercranial germ cell tumors, and mediastinal B-cell lymphoma, comprising a step of providing a crystalline avapritinib as defined in claim 1 to a person in need of such a treatment.

* * * * *